(12) United States Patent
Watters et al.

(10) Patent No.: US 7,986,218 B2
(45) Date of Patent: *Jul. 26, 2011

(54) SENSOR DEVICES FOR STRUCTURAL HEALTH MONITORING

(75) Inventors: David G. Watters, Sunnyvale, CA (US); David L. Huestis, Menlo Park, CA (US); Alfred J. Bahr, Mountain View, CA (US); Namal Priyantha, Mountain View, CA (US); Palitha Jayaweeera, Fremont, CA (US)

(73) Assignee: Yasumi Capital, LLC, Wilmington, DE (US)

( * ) Notice: Subject to any disclaimer, the term of this patent is extended or adjusted under 35 U.S.C. 154(b) by 976 days.

This patent is subject to a terminal disclaimer.

(21) Appl. No.: 11/326,224

(22) Filed: Jan. 4, 2006

(65) Prior Publication Data
US 2006/0170535 A1 Aug. 3, 2006

Related U.S. Application Data

(63) Continuation of application No. 10/115,872, filed on Apr. 3, 2002, now Pat. No. 7,034,660, which is a continuation-in-part of application No. 09/258,073, filed on Feb. 26, 1999, now Pat. No. 6,806,808.

(51) Int. Cl.
*H04Q 5/22* (2006.01)
(52) U.S. Cl. ........................ 340/10.41; 340/665; 324/693
(58) Field of Classification Search ............... 340/10.4, 340/10.41, 10.1, 10.2, 10.3, 539.1, 870.07; 324/693
See application file for complete search history.

(56) References Cited

U.S. PATENT DOCUMENTS

| 2,902,560 A | 9/1959 | Stanbeck et al. |
| 3,098,136 A | 7/1963 | Stanbeck et al. |

(Continued)

FOREIGN PATENT DOCUMENTS

| CH | 198991 | 9/1937 |

(Continued)

OTHER PUBLICATIONS

SPIE *Web*, Engineers turn Vermont bridge into world's "smartest", Apr. 17, 2002, Industry Focus, http://www.spie.org/web/oer/november/nov97/vermont.html.

(Continued)

*Primary Examiner* — Brian A Zimmerman
*Assistant Examiner* — Nabil H Syed

(57) ABSTRACT

Described herein are wireless interrogation systems and methods that rely on a complementary sensing device and interrogator. The sensing device is disposed to measure a parameter indicative of the health of a structure. A sensor reading from the sensor indicates the level of a parameter being monitored or whether one or more particular physical or chemical events have taken place. Using wireless techniques, the interrogator probes the device to determine its identity and its current sensor reading. This often includes transmission of a wireless signal through portions of the structure. When activated, the device responds with a wireless signal that identifies the device and contains information about the parameter being measured or a particular sensor state corresponding to the parameter. The identity of the device allows it to be distinguished from a number of similar devices. Thus this invention finds particular usefulness in the context of an array of devices that can be probed by a wireless interrogation unit. In one embodiment, the devices are passive and derive power from the interrogation signal.

27 Claims, 16 Drawing Sheets

U.S. PATENT DOCUMENTS

| | | | |
|---|---|---|---|
| 3,911,434 A | 10/1975 | Cook | |
| 4,213,292 A | 7/1980 | Dolezal et al. | |
| 4,500,213 A | 2/1985 | Grimm | |
| 4,616,199 A | 10/1986 | Oster | |
| 4,646,066 A | 2/1987 | Baughman et al. | |
| 4,762,426 A | 8/1988 | Foss | |
| 4,764,244 A | 8/1988 | Chitty et al. | |
| 4,800,128 A * | 1/1989 | Schacht et al. | 428/448 |
| 4,891,255 A | 1/1990 | Ciarlo | |
| 4,930,127 A | 5/1990 | Abaziou et al. | |
| 5,053,774 A | 10/1991 | Schuermann et al. | |
| 5,114,504 A | 5/1992 | AbuJudom, II et al. | |
| 5,181,423 A | 1/1993 | Philipps et al. | |
| 5,211,129 A | 5/1993 | Taylor et al. | |
| 5,214,409 A | 5/1993 | Beigel | |
| 5,218,343 A | 6/1993 | Stobbe et al. | |
| 5,278,806 A | 1/1994 | Affolter | |
| 5,300,875 A | 4/1994 | Tuttle | |
| 5,310,999 A | 5/1994 | Claus et al. | |
| 5,446,452 A | 8/1995 | Litton | |
| 5,448,220 A | 9/1995 | Levy | |
| 5,452,262 A | 9/1995 | Hagerty | |
| 5,461,385 A | 10/1995 | Armstrong | |
| 5,461,985 A | 10/1995 | Gersemsky | |
| 5,481,262 A | 1/1996 | Urbas et al. | |
| 5,499,017 A | 3/1996 | Beigel | |
| 5,531,823 A | 7/1996 | Breton | |
| 5,532,932 A | 7/1996 | Niwa | |
| 5,585,554 A | 12/1996 | Handfield | |
| 5,591,974 A | 1/1997 | Troyer et al. | |
| 5,680,106 A | 10/1997 | Schrott et al. | |
| 5,691,698 A | 11/1997 | Scholl et al. | |
| 5,712,609 A | 1/1998 | Mehregany et al. | |
| 5,717,135 A | 2/1998 | Fiorletta et al. | |
| 5,728,933 A | 3/1998 | Schultz et al. | |
| 5,745,039 A | 4/1998 | Hof et al. | |
| 5,745,049 A | 4/1998 | Akiyama et al. | |
| 5,764,138 A | 6/1998 | Lowe | |
| 5,792,337 A | 8/1998 | Padovani et al. | |
| 5,822,714 A | 10/1998 | Cato | |
| 5,825,302 A | 10/1998 | Stafford | |
| 5,833,603 A | 11/1998 | Kovacs et al. | |
| 5,850,181 A | 12/1998 | Heinrich et al. | |
| 5,861,809 A | 1/1999 | Eckstein et al. | |
| 5,883,582 A | 3/1999 | Bowers et al. | |
| 5,895,843 A | 4/1999 | Taylor et al. | |
| 5,946,179 A | 8/1999 | Fleege et al. | |
| 5,949,342 A | 9/1999 | Frary et al. | |
| 5,963,121 A | 10/1999 | Stygar et al. | |
| 5,966,066 A | 10/1999 | Mehregany et al. | |
| 5,996,413 A | 12/1999 | Iyer et al. | |
| 6,078,269 A | 6/2000 | Markwell et al. | |
| 6,100,788 A | 8/2000 | Frary | |
| 6,105,430 A | 8/2000 | Kepler et al. | |
| 6,119,526 A | 9/2000 | Reigstad et al. | |
| 6,124,810 A | 9/2000 | Segal et al. | |
| 6,129,824 A | 10/2000 | Rollick et al. | |
| 6,254,548 B1 | 7/2001 | Ishikawa et al. | |
| 6,259,372 B1 | 7/2001 | Taranowski et al. | |
| 6,352,466 B1 | 3/2002 | Moore | |
| 6,617,963 B1 | 9/2003 | Watters | |
| 6,770,190 B1 * | 8/2004 | Milanovski et al. | 205/777.5 |
| 6,806,808 B1 | 10/2004 | Watters et al. | |
| 2002/0180609 A1 * | 12/2002 | Ding et al. | 340/633 |
| 2003/0159946 A1 * | 8/2003 | Eden et al. | 205/777.5 |
| 2004/0124858 A1 * | 7/2004 | Srinivasan et al. | 324/693 |

FOREIGN PATENT DOCUMENTS

| | | |
|---|---|---|
| CH | 610 178 G | 4/1979 |
| EP | 11153568 | 8/1999 |
| GB | 2308947 | 7/1997 |
| JP | 61-141098 | 6/1986 |
| JP | 05-288708 | 11/1993 |
| JP | 06-039330 | 2/1994 |
| JP | 07-27256 | 5/1995 |
| JP | 08-226966 | 9/1996 |
| JP | 09-171012 | 6/1997 |
| JP | 10-227702 | 8/1998 |
| JP | 11/153568 | 6/1999 |
| JP | 11-344572 | 12/1999 |
| JP | 2000-028567 | 1/2000 |
| JP | 2000-146899 | 5/2000 |
| JP | 2001-513881 | 9/2001 |
| JP | 2001-291181 | 10/2001 |
| WO | WO94/27117 | 11/1994 |
| WO | WO 94/27117 | 11/1994 |

OTHER PUBLICATIONS

C.L. Britton, Jr., et al., "MEMS Sensors and Wireless Telemetry for Distributed Systems", Mar. 1998, SPIE vol. 3328.

P. Neuzil, et al., "An Integrated Circuit to Operate a Transponder with Embeddable MEMS Microsensors for Structural Health Monitoring", 1997, Structual Health Monitoring, Session 1 pp. 492-501.

B. Westermo, et al., "A Peak Strain Sensor for Damage Assessment and Health Monitoring", 1997, Structual Health Monitoring, Session 1 pp. 515-526.

Kovacs, Gregory T.A., *Micromachined Tranducers Sourcebook*, 1998.

Watters, David G., et al., Subsurface Microsensors for Automated Re-Certification of Thermal Protection Systems (SMARTPS): A Rapid Wireless Inspection Method, *SRI Project 2437*, Final Report, Sep. 1998.

Krantz, Donald, et al., Applied Research in Remotely-Queried Embedded Microsensors, *SPIE*, vol. 3328, Mar. 1998.

Abtech Scientific, Inc. "Interdigitated Microsensor Electrodes(IMEs)", website printout from www.abtechsci.com/imes.html, Last Revised Jul. 25, 2000, 4 pages.

Press Release, "World's First RFID Tagging IC with Sensor Input Targets Industrial Applications," Microchip, Microchip Website, http:\\www.microchip.com/10/edit/pRelease/pr120/index.htm.

Watters et al, U.S. Appl. No. 09/258,073, "Wireless Event-Recording-Devices With Identification Codes", filed Feb. 26, 1999.

MCRF202, "Passive RFID Device With Sensor Input," Microchip, *1999 Microchip Technology, Inc.*, pp. 1-8.

Watters et al, U.S. Appl. No. 09/514,960, "Reusable Launch Vehicle Health Maintenance", filed Feb. 29, 2000.

Watters et al, U.S. Appl. No. 09/513,327, "Event-Recording Devices With Identification Codes", filed Feb. 25, 2000.

Taub et al., "Principle of Communication Systems", 0971, McGraw-Hill, $1^{st}$ edition, pp. 227-228.

NASA Jet Propulsion Laboratory, "Automated Cargo—T-racking Transponders", *NASA Tech Briefs*, Sep. 1998.

Robert Puers, "Linking Sensors with Telemetry: Impact on the System Design", *Transducers, Eurosensors IX*, 1995, 4A-1.

Akin et al., "An Implantable Multichannel Digital Neural Recording System for a Micromachined Sieve Electrode", *Transducers, Eurosensors IX*, 5-Al, 1995.

Koenraad Van Schuylenbergh et al., "Self-Tuning Inductive Powering for Implatable Telemetric Monitoring Systems", *Transducers, Eurosensors IX*, 6 A-1, 1995.

Dino R. Ciarlo, "A Latching Accelerometer Fabricated by the Anisotropic Etching of (110) Oriented Silicon Wafers", *J. Micromech, Microeng.*, 1992, pp. 10-13.

Gregory T.A. Kovacs, *Micromachined Tranducers Sourcebook*, 1998.

Web pages from website www.shuttle.nasa.gov/shuttle/reference/sodb/2-5b.pdf, 2 pages.

Zhang et al., "Thermally Actuated Microprobes for a New Wafer Probe Card", *IEEE Journal of Microelectromechanical Systems*, V. 8, No. 1 (Mar. 1999).

Goldman et al., "A Novel Micromechanical Temperature Memory Sensor", *Transducers 95-Eurosensor IX*, pp. 132-135.

Carr et al., "Integrated Pressure Sensor with Remote Power Source and Remote Readout", *Transducers 95-Eurosensor IX*, pp. 132-135.

Texas Instruments RFID Products-Document Center-S2000 References Manual, Series 2000 Reader System, Control Module Hardware, RI-CTL-MB2A, RI-CTL-MB6A, Jan. 1998.

Cragun et al., "Linear Thermomechanical Microactuators", *Mechanical Engineering Department*, Brigham Young University.

Richard P. Feynman, "Excerpt from 'Its Plenty of Room at the Bottom", *Engineering and Science*, California Institute of Technology, 1960.

Goldman et al., "A Novel Micromechanical Temperature memory Sensor", *8th International Conference on Solid-State Sensors and Actuators and Eurosensors 1X*, Jun. 25-29, 1995.

The International Search Report for PCT/US2003/09644 mailed on Aug. 13, 2003.

The International Search Report for PCT/US2000/04998 mailed on Jul. 26, 2000.

The Written Opinion for PCT/US2000/04998 mailed on Dec. 8, 2000.

The International Preliminary Examination Report for PCT/US2000/04998 mailed on May 14, 2001.

English translation of Office Action issued in Japanese Patent Application No. 2003-582501 dispatched Dec. 12, 2008.

Decision of Rejection for Japanese Patent Application No. 2003-582501 dispatched on Jun. 30, 2009. (English translation provided).

Office Action for Japanese Patent Application No. 2000-601400 dated Oct. 16, 2009. English translation not readily available.

Final Office Action for Japanese Application No. 2000-601400 dated Mar. 2, 2010.

EP Communication issued in European Patent Application No. 00917673.6 and dated Jun. 29, 2010.

EP Communication issued in European Patent Application No. 03 716 889.5 and dated Sep. 13, 2010.

* cited by examiner

SENSOR DEVICES FOR STRUCTURAL HEALTH MONITORING

CROSS-REFERENCE TO RELATED APPLICATIONS

This application is a continuation application of U.S. patent application Ser. No. 10/115,872, filed Apr. 3, 2002 and entitled, "SENSOR DEVICES FOR STRUCTURAL HEALTH MONITORING" (now U.S. Pat. No. 7,034,660), which is incorporated herein for all purposes and which is a continuation-in-part application of U.S. patent application Ser. No. 09/258,073 filed on Feb. 26, 1999 (now U.S. Pat. No. 6,806,808), which is incorporated by reference herein.

BACKGROUND OF THE INVENTION

The present invention relates generally to sensor technology. More particularly, the present invention relates to sensing devices and systems used to monitor large structures using wireless communication techniques.

Many large structures are prone to degradation over time. For example, a large structure including metal elements, such as an aircraft or concrete structure with metal reinforcement, is often susceptible to metal corrosion. Active monitoring and maintenance of a structure may alleviate degradation. Conventional sensing techniques frequently do not provide suitable monitoring solutions for monitoring the health of a large structure. For a concrete structure with metal reinforcement, the metal is often embedded within the structure and inaccessible using sensors that employ a wire for external communication. In some applications, the structure may be so large that hundreds or thousands of sensors are needed for health observation and information collection. For structures comprising concrete for example, concrete strength and lifetime performance are strongly dependent on curing conditions. Construction personnel would ideally like to monitor the temperature of discreet points within the concrete during the curing process. This is not permissible according to conventional techniques.

Inspection of aging bridge decks, as another example, is an important component of an effective highway maintenance program. Pavement and concrete exposed to heavy traffic and weathering deteriorate over time. There are an abundant number of bridges (about 600,000) in United States—and California alone has over 12,000 bridges. Each bridge is inspected on a regular basis. Most of the bridges include metal elements such as tensile bars and metal grids embedded in the concrete. Chloride from the environment surrounding the bridge diffuses into the concrete at its surface, and diffuses from the surface into the concrete depths. The chloride ions may originate from deicing salts in cold climates or salt water from seawater spray in coastal zones, or runoff from nearby (salty) soil embankments, for example. Over time, the amount of chloride in the concrete increases and may reach levels that substantially attack and corrode the metal elements. For a given metal, there is typically a chloride concentration level where corrosion initiates. Steel rebar for example will corrode in the presence of chloride ions at known critical levels. The resulting corrosion leads to expansion of the rebar volume and cracking of the concrete. Monitoring corrosion of the metal caused by chloride ingress is a major objective of regular highway maintenance inspections. Since the metal bars and grids are usually embedded within the concrete at a particular depth, chloride levels at varying depths of the concrete may be monitored to track chloride ion ingress and to detect when chloride presence in the concrete is approaching levels of interest.

Current inspection techniques include visual observation and manual extraction of core samples. Highway engineers frequently take core samples and submit them for laboratory analysis to determine chloride penetration. This process typically involves removing a cylindrical plug from the concrete. Highway engineers then send the plug to a lab and wait for results. Laboratory analysis involves slicing the sample into layers, crushing individual layers, dissolving the layers into solution, followed by a multi-step titration process to determine the chloride concentration. In addition to performing this analysis, individual samples need to be labeled and tracked to correlate lab measurements with specific bridges.

Not only highly time-consuming, costly, and prone to confusion, this method also aggravates the same problem it intends to detect and prevent. Namely, highway engineers refill the hole with a plug. Given the inevitable mismatch of plug materials and sizing, chloride ions now have an easier route into the concrete depths. These manual techniques may also contribute to traffic congestion. Moreover, it typically takes years for a critical chloride concentration to be reached, so a large number of these inefficient manual tests may be required.

In view of the foregoing, there are desired improved structures and techniques for monitoring the health of large structures, such as bridge decks.

SUMMARY OF THE INVENTION

The present invention improves structural health monitoring by enabling wireless interrogation systems and methods that rely on a complementary sensor device and interrogator. The sensor device comprises a sensor that measures a parameter indicative of the health of the structure. A sensor reading from the sensor indicates the level of a parameter being monitored or whether one or more particular physical or chemical events have occurred. For example, the device may include an electrochemical sensor that measures the level of a chemical species in the structure and an event may be the attainment of a particular concentration level of the chemical species. Using wireless techniques, the interrogator probes the sensor device to determine its identity and a current sensor reading or state. Often, the sensor device is embedded in the structure and transmission of a wireless signal occurs through a portion of the structure. When activated, the device responds with a wireless signal that identifies the device and contains information about the parameter being measured or a particular sensor state. The identity of the device allows it to be distinguished from a number of similar devices. Thus this invention finds particular usefulness in the context of an array of devices that can be probed by a wireless interrogation unit. In one embodiment, the devices are passive and derive power from the interrogation signal.

In one aspect, the present invention is applied to monitoring the health of roadways, bridges or portions thereof such as bridge decks. A device comprising a sensor is embedded in the concrete and measures local chloride concentration. When polled by a suitable interrogator, the device outputs a signal corresponding to the chloride concentration. For example, the interrogator may pole the device using an RF signal. Using circuitry that quickly responds to the interrogation signal, the present invention enables real-time communication with an embedded sensor. Each device may be uniquely identified with a number or code stored in a microchip, for example. Interrogation of numerous devices in proximity may use anticollision algorithms and RFID technology. A database may be constructed for a sensor array in a roadway or bridge. The database may be used to track polling results over time for a single bridge—and allow for convenient comparison of the health status for numerous bridges. Applying interrogation to hundreds and thousands of bridges provides an automated and simplified tool to help maintenance technicians prioritize maintenance schedules for a large number of bridges. In one embodiment, the devices are passive and derive power from the RF illumination, thereby alleviating the need for battery power and battery maintenance so that the embedded sensor devices may last as long as the bridge or bridge deck.

Real-time communication with an embedded sensor permits the interrogator to be placed on a truck or moving vehicle, and polling of numerous similar devices embedded in multiple locations of a bridge deck to be performed as the truck drives over each device. For roadway maintenance programs, vehicular interrogation in this manner offers simplified and expeditious polling compared to conventional manual techniques.

In one embodiment, a hand-held RF interrogator illuminates a local region of a structure, powering any embedded sensors in the region and obtaining sensor data from the sensors. Data may be provided by the sensor in various forms. For example, sensors may provide overlimit or threshold data that indicate when a parameter, such as a concentration level of an aggressive chemical or species in the structure, has reached a level of interest. Some parameters measured by sensor devices of the present invention include concentration levels, pH, conductivity, epoxy moisture ingress, corrosion of a surrogate, and polarization resistance, for example. By combining sensor feedback with known sensor device position in the structure and sensor data history, changes in the parameter may be tracked over time. Information collection in this manner applied over an entire structure allows a profile of health progression in the entire structure, e.g., the profile of chemical ingress in a bridge deck.

To keep the sensor device small and simple, it may be passive—that is, it does not require a self-contained continual power source for operation (such as a battery). This also extends device longevity. Thus, components included in the device such as a sensor and transponder may be passive. In one example described, a radio frequency interrogation signal may provide the transponder power.

In one aspect, the present invention relates to a device comprising a sensor that detects a parameter indicative of the health of a structure comprising a metal. The device also comprises a transponder in electrical communication with the sensor and that transmits a wireless signal through a portion of the structure indicating the parameter status when triggered by a wireless interrogation signal. The device further comprises an identification source in electrical communication with the transponder that uniquely identifies the device.

In another aspect, the present invention relates to a device disposed in a structure comprising concrete. The device comprises a sensor embedded in the concrete that detects a parameter. The device also comprises a transponder in electrical communication with the sensor and that transmits a wireless signal through a portion of the concrete indicating the parameter status. The device further comprises an identification source in electrical communication with the transponder that uniquely identifies the device.

In yet another aspect, the present invention relates to a device comprising an electrochemical cell that measures the potential difference between a reference electrode and an ion selective electrode. The device also comprises an identification source that uniquely identifies the device. The device further comprises a transponder in electrical communication with the electrochemical cell and in electrical communication with the identification source that transmits a wireless signal indicating the potential difference and information from the identification source.

In still another aspect, the present invention relates to a device for monitoring the health of a bridge comprising concrete and a metal. The device comprises a sensor, at least partially exposed to the concrete, that detects chloride presence in the concrete. The device also comprises a transponder in electrical communication with the sensor and that transmits a wireless signal through the concrete indicating the level of chloride when triggered by a wireless interrogation signal. The device further comprises an identification source in electrical communication with the transponder that uniquely identifies the device. The device is passive.

In another aspect, the present invention relates to a system for reporting the health of a bridge comprising concrete and a metal. The system comprises an array of devices, each of which is embedded in the bridge. Each device has a sensor that detects a parameter indicative of the health of the bridge, a transponder in electrical communication with the sensor and that transmits a wireless signal through a portion of the concrete indicating the parameter status when triggered by a wireless interrogation signal, and an identification source in electrical communication with the transponder that uniquely identifies each device from the other devices. The system also comprises an interrogator for externally probing a device in the array to determine the parameter status. The interrogator is designed or configured to read the parameter status by (i) providing the wireless interrogation signal to the transponder and (ii) receiving a wireless response from the device.

In another aspect, the present invention relates to a method for monitoring the health of a structure comprising concrete and a metal. The method comprises embedding a sensor device in the concrete. The sensor device comprises a sensor that detects a parameter indicative of the health of the structure, an identification source that can distinguish the device from the other similar devices, and a transponder. The method also comprises detecting a parameter status using the sensor. The method further comprises probing the device with an interrogator that produces a wireless signal that transmits through a portion of the concrete. The method additionally comprises returning a wireless signal from the device through a portion of the concrete. The return wireless signal indicates the parameter status. In one embodiment, the structure is a bridge or a portion of a bridge.

The present invention finds use in a wide range of applications. The use of an identification code with each recording device allows for monitoring large structures having many spatially separated points that are to be individually monitored.

These and other features and advantages of the present invention will be described in the following description of the invention and associated figures.

DETAILED DESCRIPTION OF THE PREFERRED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

Structural Health Monitoring

Figure 1A:
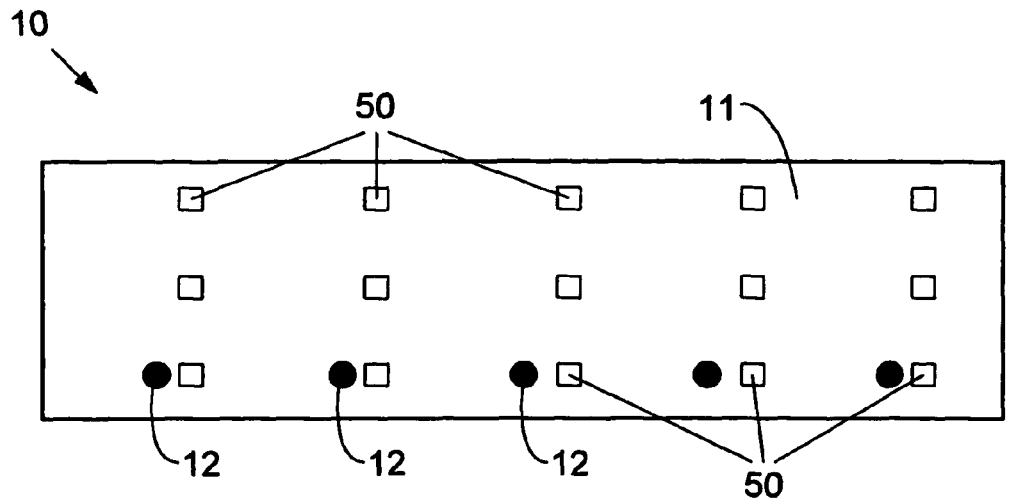
FIG. 1A illustrates a structure portion comprising concrete and metal and an array of sensing devices of the present invention.

The present invention is well suited to monitor the health of a large structure or portion thereof. FIG. 1A illustrates a structure portion 10 may be included as part of a building, bridge, road, etc and comprises concrete 11 and metal 12. An array of sensing devices 50 are embedded in structure portion 10 and detect a parameter indicative of the health of structure portion 10. Sensor devices 50 detect and report physical or chemical parameters, events or states where multiple points of interest are to be monitored. Each such point is associated with a separate sensing device of this invention. Together the devices 50 form a sensor array. Preferably, each sensor device of such array has a unique identifier that uniquely identifies the device from other similar devices and permits the device to provide a suitable distinguishable reading when probed.

The wireless monitoring techniques of the present invention are suitable for health monitoring of various structures. As the term is used herein, a structure generally refers to anything that has been constructed. Exemplary structures that are monitored according to various embodiments of the present invention include roads, bridges, buildings, railroad tracks, aircraft, pipelines, tunnels, spacecraft, storage tanks, nuclear power plants, and theme-park rides. The buildings may include structures such as parking garages, office buildings, sea walls, etc. Railroad tracks may comprise metal and wood designs or metal and concrete designs, for example. Structure as defined herein also includes structural portions and components of a structure such as individual walls and layers, road and bridge components such as a bridge deck etc. The structures may comprise any suitable materials such as concrete, wood, cement or mortar, asphalt or asphalt concrete, structural honeycomb, glues, liquids (stationary or flowing), plastics, soils, or inaccessible compartments of complex structures such as aircraft or trains, etc. A sensor device of the present invention may be variably located, attached to, or embedded in any of these non-metal materials. As the term is used herein, concrete is intended to refer to any material comprising a conglomerate gravel, broken stone, or slag in a mortar or cement matrix. Two common conventional forms of concrete used for roadways are Portland cement concrete and asphalt concrete. Devices may also be embedded into a variety of non-metallic materials such as dielectric, lossy dielectric, or even metal coated materials (so long as the thickness of the metal coat is much less than the skin depth of the material at the wavelength of the interrogation). In addition to the above-mentioned applications, sensor devices of the present invention are generally applicable to any application where rapid or remote inspection of large structures is useful.

Generally, sensor devices of this invention detect a physical "parameter". The parameter is usually a physical or chemical property of an item such as its temperature, density, strain, deformation, acceleration, pressure, mass, opacity, concentration, chemical state, hardness, conductivity, resistance, magnetization, dielectric constant, size, etc. The parameter is typically indicative of the health of the structure, or a portion thereof. For example, stress or strain in various portions of the structure can be used to indicate structural health. Alternatively, the parameter or physical property may relate to some form of structural degradation or threat, such as the presence of a chemical that attacks the structure or an element included therein. The item whose parameter is being monitored may be included in the structure (e.g., detecting resistance and corrosion of a metal element included in a bridge deck) or added to the structure (e.g., detecting resistance and corrosion of a surrogate metal included in a sensor device that physically or chemically mimics a metal element included in a bridge deck). For monitoring the health of a metal used in a bridge or bridge portion for example, the parameter may correspond to chemical concentration, pH, conductivity, corrosion levels, and polarization resistance. In this case, the item being monitored may correspond to a metal element in the bridge or a surrogate item added to the bridge for monitoring purposes.

Health of a structure generally refers to any condition or physical parameter pertinent to the functionality of the structure. This includes the health of portions and components included in the structure such as separately constructed portions, individual materials, reinforcement beams, cables and bars that contribute to structural integrity, adhesives, seals, joints, fasteners, etc. In many cases, a failure mode of the structure is linked to a parameter being sensed by a sensor of the present invention. Pavement and concrete exposed to weathering and heavy traffic degrades with time. Pavement failure modes include overstress, over strain, temperature induced curling and deflection, and corrosive attack on metal components within the roads and bridges such as metal bars and metal grades, for example. A sensor device may be embedded in concrete to detect each of these conditions. In the last case, the present invention may detect the levels of aggressive species responsible for corrosion of the metal components.

In some cases, a sensor device detects an "event" associated with a parameter. The physical or chemical event may correspond to attainment of a particular value of the physical property. For roadway inspection applications, the event may correspond to reaching a particular threshold concentration level within the concrete for a chemical aggressive to metal embedded in the concrete. Alternately, a physical event may correspond to reaching a particular threshold temperature or humidity level within concrete during curing. Another physical event may be a change of state such as a phase change in the item being sensed. Examples of phase changes include transformations between gas, liquid, and solid states, changes in morphology (e.g., crystalline state), magnetization, and the like.

In one embodiment, sensing devices of the present invention may be employed to measure overstress thresholds in concrete using a piezoelectric sensor device that is powered by an interrogating RF illumination. These pressure sensitive devices may be manually inserted at the asphalt concrete subgrade interface, at the base of the subgrade, or in load transfer dowels as a part of a dowel retrofit program (see FIG. 2C). At convenient and subsequent times, a wireless interrogator illuminates regions within the concrete and pavement, power the embedded wireless sensor devices, and obtain the tensile and compressive stressed data. For an array of sensing devices embedded in the concrete, each device may return its own identification code and the desired parameter being sensed. For example, each device may return a signal that indicates whether or not stress in the concrete has exceeded some over limit condition (such as 400 psi tensile stress in concrete). If so, further validation tests on the concrete may be performed.

The present invention is also suitable for detecting multiple parameters and events. The multiple parameters and events may be associated with multiple parameters, multiple thresholds for the same parameter, or a combination thereof. For example, the physical or chemical events may be different threshold concentration levels of chloride in concrete 11 of FIG. 1A.

Note that the parameter or event to be detected could be a very fast or instantaneous event or one that requires a significant time to unfold. An example of this latter case is reaching a particular chemical concentration level in concrete, which may take years. A time-integrated exposure by the event-recording device may be appropriate for long term monitoring. In this manner, detection of a new steady state condition along a continuum of values can be detected and reported.

Wireless sensing devices of the present invention are well-suited for embedding within concrete to monitor the health of structures comprising concrete. In one embodiment, the devices monitor a parameter during curing of the concrete, such as temperature, pressure, or humidity. Concrete strength and lifetime performance are highly dependent on curing conditions. This is especially true for high-performance concrete. Knowledge of curing conditions enables construction personnel to estimate lifecycle cost, plan maintenance actions, and perform quality control on new construction. In a specific embodiment, a sensor device 50 embedded in concrete obtains local temperature measurements at periodic intervals during curing. When polled by an interrogator of the present invention, the devices respond with (or without) temperature data that they are configured to detect. Sensors disposed to detect humidity may monitor a hydration process of curing concrete. Low-cost wireless temperature sensors of the present invention may be widely distributed in a new construction, enabling a thorough evaluation of cure integrity. In some cases, these devices may include a small battery that provides DC power and may be polled by an RF interrogator periodically for 28 days after the pour. As a result of the measured data, construction personnel may verify cure integrity in a structure and identify spatially distribute regions that may require more careful inspection, or rework.

As mentioned before, there is typically a critical chloride concentration level where corrosion initiates for a given metal. Correspondingly, a sensor device 50 of the present invention may be embedded in a structure comprising concrete and a metal (e.g., reinforced concrete) to detect a chloride concentration threshold level, and/or one or more intermediate concentration threshold levels useful for tracking chloride build up to the critical chloride concentration level. Thus, multiple sensor devices 50 may be embedded within structure 10 to determine the amount and profile of chloride penetration in structure 10.

Other applications monitor corrosion detection (in bridges and aircraft for example) by detecting a threshold change in conductivity (e.g., corrosion of a material of interest breaks a circuit connection); water absorption detection (by a hydroscopic material for example) by detecting a change in EMF, conductivity, ion detection (by precipitation of an insoluble species such AgCl for chloride detection) by detecting a change in opacity, for example. Note that for many of these applications, the parameter being detected involves a level of exposure. The device reports how much exposure has occurred. The value of conductivity, opacity, absorption, etc., correlates to the level of exposure and the sensor device can report this level.

2. Road and Bridge Health Monitoring Systems

In particular, the present invention is suitable for periodic health monitoring of roads and bridges. Inspection of aging pavement and concrete is an important component of most highway maintenance programs. Although the present invention will now be described primarily with respect to monitoring the health of bridge decks and concrete based structures, the present invention is not limited to these structures and materials and is not intended to be limited by examples provided in the expansion of this embodiment.

Figure 1B:
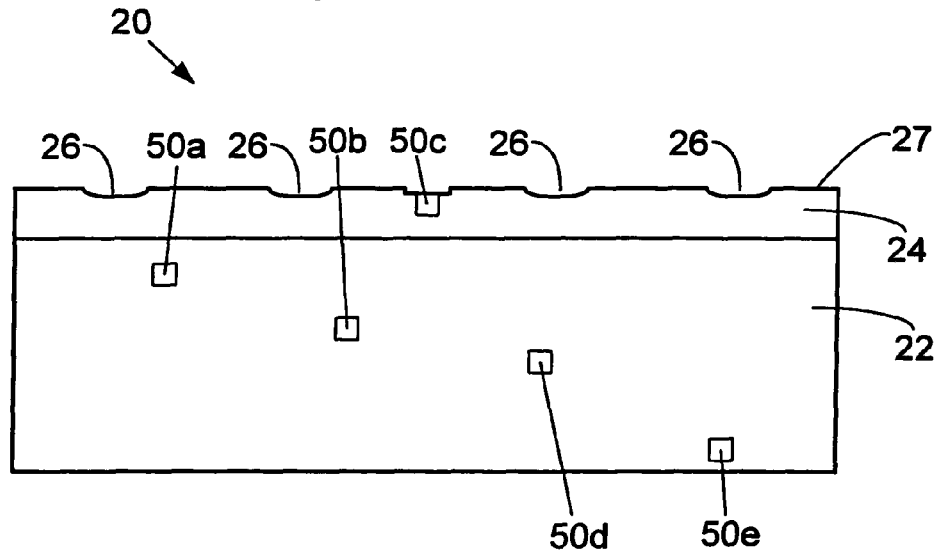
FIG. 1B illustrates a cross-section of roadway including an array of sensing devices in accordance with one embodiment of the present invention.

FIG. 1B illustrates a cross-section of roadway 20 including an array of sensing devices 50 in accordance with one embodiment of the present invention. Roadway 20 includes a dual layer construction comprising Portland cement concrete 22 disposed below asphalt concrete 24. Devices 50 are embedded at various locations within concrete 22 and concrete 24. For example, devices 50a and 50b are laterally disposed to align with wheel paths 26 and monitor degradation of roadway 20 in these vertical regions. Device 50c is disposed in the lateral midsection of roadway 20 and close to the surface 27. Devices 50a-50e are disposed at varying depths of roadway 20. Devices 50a and 50b are embedded at the upper and lower surfaces of the interface between Portland cement concrete 22 and asphalt concrete 24, respectively. Devices 50c and 50d are embedded deep within Portland cement concrete 22.

Figure 2A:
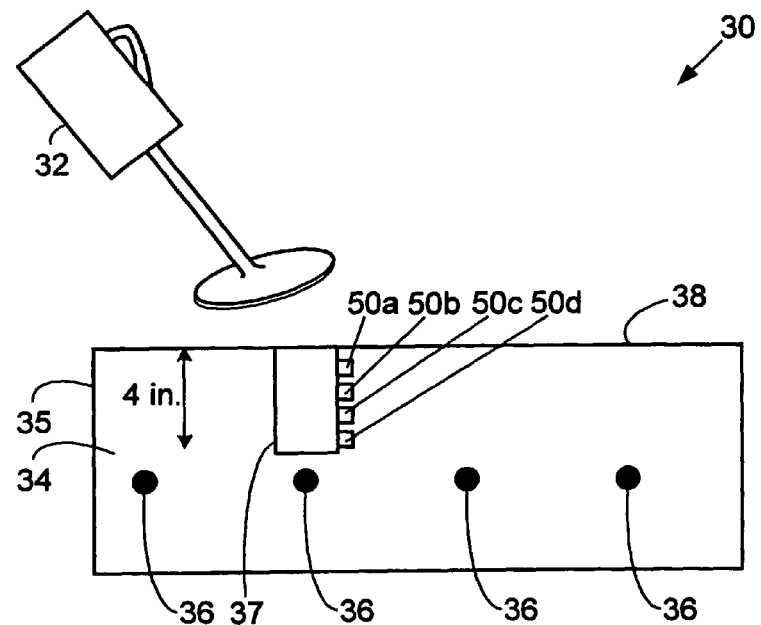
FIG. 2A is an illustrative representation of a sensor system for monitoring a bridge deck cross-section in accordance with one embodiment of the present invention.
Figure 2B:
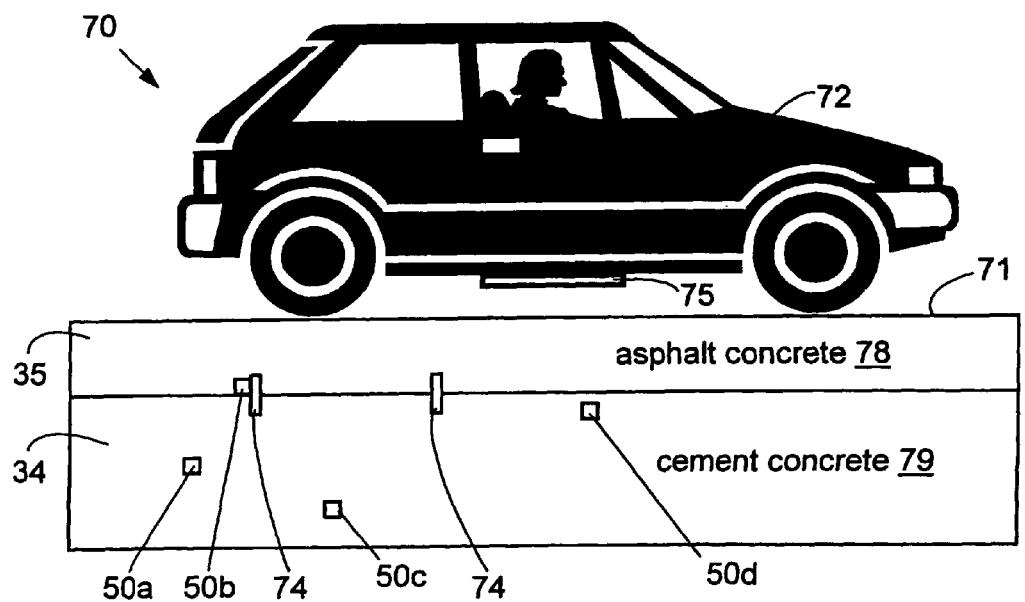
FIG. 2B illustrates a sensor system comprising an interrogator carried by a moving vehicle in accordance with another embodiment of the present invention.

FIGS. 2A-2B illustrate a wireless inspection system for monitoring the health of road structures in accordance with embodiments of the present invention. FIG. 2A is an illustrative representation of a sensor system 30 for monitoring a bridge deck 35 cross-section in accordance with one embodiment of the present invention. Rebars 36 are disposed in concrete 34 included in bridge deck 35. Chloride penetration from the surface 38 of bridge deck 35 may contribute to metal corrosion of rebars 36.

Figure 4A:
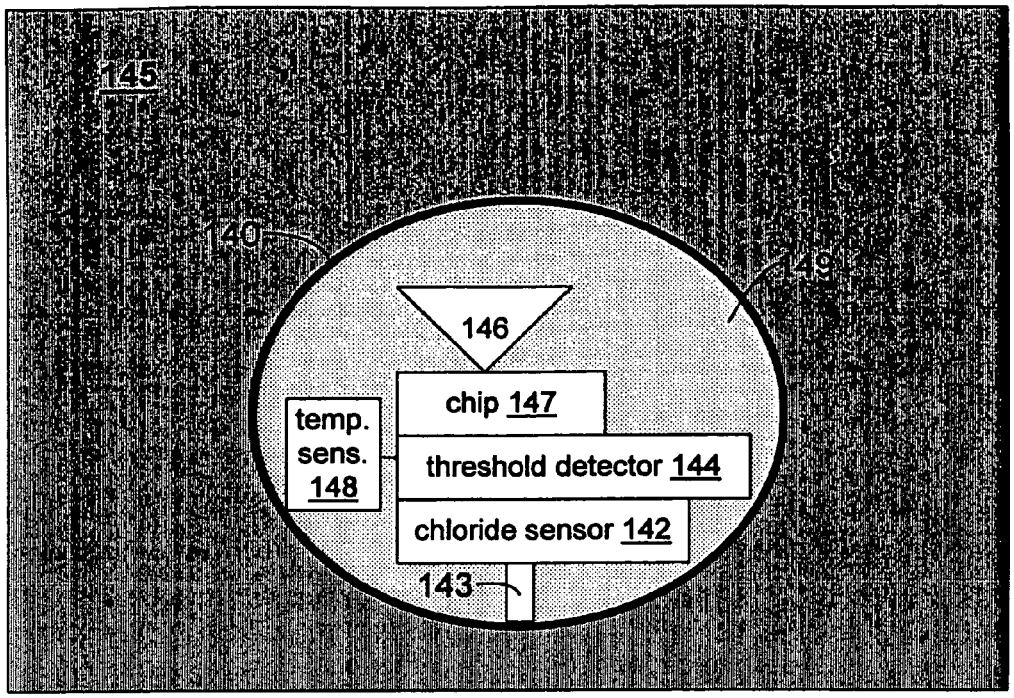
FIG. 4A illustrates a simplified cross-section view of a chloride ion sensor device in accordance with one embodiment of the present invention.

Sensor devices 50 are embedded within bridge deck 30. As shown, devices 50 are embedded within bridge deck 30 using a back-filled core 37. In a specific embodiment, each device has an operational depth at a one-inch increment below surface 38. More specifically, device 50a has an operational depth one inch below the surface of bridge deck 35, device 50b has an operational depth two inches below the surface of bridge deck 35, device 50c has an operational depth three inches below the surface of bridge deck 35, etc. The operational depth refers to the fact that device 50 may be directionally dependent and have a particular portion responsible for sensing and interface with the surrounding structure. In one embodiment, device 50 includes a port that limits sensor detection to a specific portion of device 50. This allows detection of a precise spatial position determined by the precise positioning and orientation of the port. For example, sensor device 50 as shown in FIG. 4A includes a chloride port that allows diffusion of chloride ions into the sensor at a particular location. For FIG. 2A, each sensor device 50 is disposed with its chloride port facing down and thus the operational depth of each sensor device is measured at the bottom of the sensor device.

System 30 relies on a hand-held or portable interrogator 32 carried by a person. Using wireless techniques, interrogator 32 communicates with sensing devices 50a-50d. Interrogator 32 produces a probing signal that penetrates portions of concrete 34 between each of the devices 50 and the current position of interrogator 32. In response to the probing signal from interrogator 32, each device 50 makes a sensor reading. Circuitry within device may convert the sensor measurement into a signal output by a transponder in the device. The transponder then returns a response signal to interrogator 32 that includes the device's ID and the sensor reading. Interrogator 32 thus allows a person to poll the embedded devices 50 and obtain chloride ingress data in a convenient manner without extracting sensor devices 50.

Devices 50 may be embedded at strategic positions within bridge deck 30 to detect and report local conditions. This implies that interrogator signals to communicate with the embedded device penetrate through the structural materials. For example, the interrogator may be designed to generate and receive RF signals that transmit through concrete. When monitoring is performed during curing of the concrete, the RF signals may also penetrate through protective plastic and plywood coverings that are used to stabilize curing conditions.

Thousands of devices 50 may be embedded in a single structure. For example, thousands of devices 50 may be embedded at varying positions of interest for a large bridge deck. The devices may be embedded in existing structures or new structures. For FIG. 2A, each device 50 is inserted into a back-filled non-concrete core for evaluation of an existing bridge. For a new bridge, device 50 may be embedded in the concrete as part of the initial concrete pour.

FIG. 2B illustrates a sensor system 70 in accordance with another embodiment of the present invention. As shown, a number of sensors 50 and dowels 74 are embedded within roadway 71. Roadway 71 is a two layer composite comprising asphalt concrete 78 disposed over Portland cement concrete 79.

Interrogator 75 is carried by a vehicle 72, such as a highway maintenance car, truck or any other suitable moving vehicle. Interrogator 75 includes an antenna disposed below the midsection of vehicle 72 that allows wireless communication with the sensors 50 embedded within roadway 71. Radio frequency power, transmitted on an RF wave from interrogator 75, is used to power wireless transponders in each sensor device 50. The radio frequency power may also be used to power a sensor and sensor reading, as well as logic in the device included in a processor or microchip. Each device 50 may then be individually powered and interrogated as vehicle 72 passes. Logic in each device may then tell the sensor device to return its identification code and a sensor reading to interrogator 75.

Typically, interrogation using interrogator 75 and vehicle 72 comprises driving the truck over roadway 71 at a suitable speed. The upper speed of vehicle 72 may depend on processing delays to send and receive a signal from a particular device 50. These delays may include a delay for a probing signal to reach a particular device 50, a delay for the device 50 to generate a response, a delay for the response signal to reach interrogator 75, and any other processing or wireless transmission delays. Regardless of the speed of vehicle 72, inspection of devices 50 using system 70 allows convenient (to highway personnel sitting in the vehicle) and less-intrusive (to traffic) methods of road health inspection.

In another embodiment, vehicle 72 includes a two-antenna system comprising a transmitting antenna at the front of the vehicle and receiving antenna disposed at the rear. The two antenna system allows a wireless device within roadway 71 to receive a probing signal from the front transmitting antenna, generate a response, and transmit a response signal back to rear receiving antenna. This two-antenna system allows for increased speed of vehicle 72 since delays in communicating with a device 50 are compensated by the distance between the front and rear antennas.

Advantageously, system 70 reduces the time and costs of roadway inspections such as bridge deck inspections. In some cases, sensor devices 50 of the present invention respond to an interrogator in the range of tens of milliseconds. Regardless of the response time of an embedded sensor device 50, the ability to probe the devices with a truck or other moving vehicle significantly reduces time and costs of bridge deck inspections for chloride ingress.

3. Principles of Operation

Figure 3A:
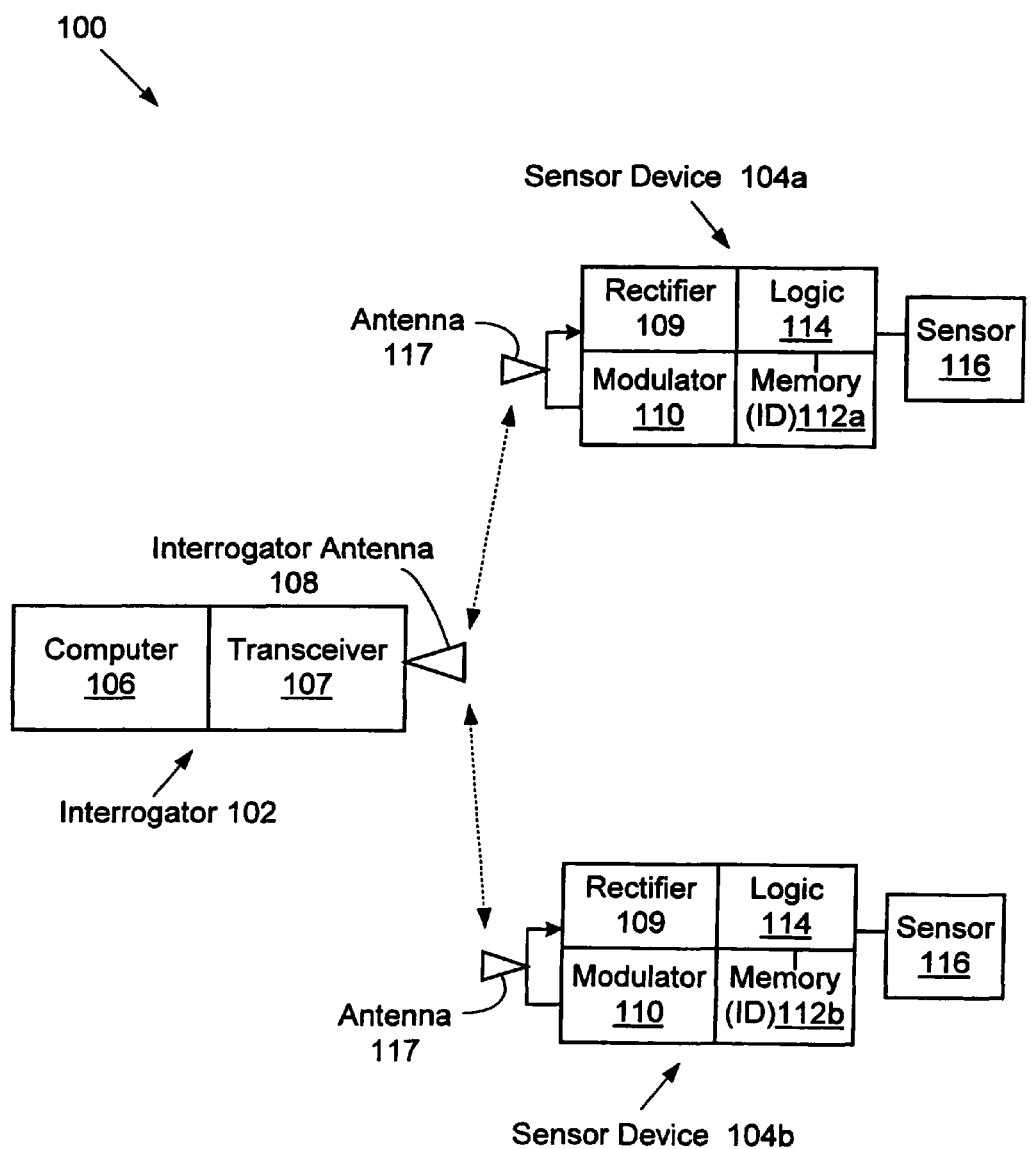
FIG. 3A illustrates a simplified sensor device system in accordance with one embodiment of the present invention.

FIG. 3A illustrates a simplified sensor device system 100 in accordance with one embodiment of the present invention. An interrogator 102 probes sensor devices 104a and 104b using wireless communication and may include any circuitry capable for performing this function. In this case, interrogator 102 includes a computer 106, a transceiver 107 and an interrogator antenna 108. In one embodiment, coupling between interrogator 102 and the individual event-recording device 104 is by radio frequency (RF) radiation.

Sensor device 104a includes rectifier 109, modulator 110, memory 112a including an identification (ID), logic 114, sensor 116, and antenna 117 (which together with modulator 110 serves as a wireless transponder).

Sensor 116 detects a parameter indicative of the health of a structure that device 104a is disposed or embedded in. Sensor 116 broadly refers to any sensor capable of detecting the intended physical or chemical parameter or event. Numerous sensors are described in further detail below. Sensor 116 outputs information corresponding to the current parameter status. Sensor 116 is preferably, but not necessarily, a passive sensor that does not require continual power. In some cases, sensor 116 may be viewed as being energized by the quantity being sensed. For example, ion concentration gradients may provide the energy to measure a voltage difference between two electrodes in an electrochemical cell. Alternatively, sensor 116 may be a wire that corrodes in the presence of a foreign chemical as described with respect to FIG. 6D.

When probed by interrogator 102, sensor device 104 replies with its ID as stored in memory 112 and information provided by sensor 116 or information from a recording mechanism that records an event. The information from sensor 116 indicates the level or status of a parameter being monitored. This information is read out along with the device's identification code. The ID code provides a mechanism for a) identifying each device 104 in a group of devices and b) automatically logging the data entry corresponding to the sensor reading of each device 104.

Logic 114 provides instructions for responding to an interrogation signal by interrogator 102 and includes circuitry and other facilities for preparing a signal to be returned from sensor device 104a. This may include processing or altering the output of sensor 116 for example. Logic 114 may be included in a commercially available microprocessor, logic device, microchip, etc.

In some embodiments, the interrogator provides power to the event-recording device and is transmitted by RF waves, for example. Rectifier 109 of sensor device 104a rectifies the signal, thereby providing DC voltage to operate components of device 104a. In one embodiment, logic 114 and rectifier 109 are included in the same microprocessor.

Sensor devices of the present invention typically comprise some form of wireless transponder for wireless communication. Generally, the transponder functions to receive and transmit wireless signals. In some cases, it automatically transmits signals when actuated or probed by a signal from an interrogator. Commonly, a transponder includes an amplifier for increasing the strength of a received incident signal (from the interrogator 102 or other actuating device), a modulator for modifying that signal with information provided to the transponder, and an antenna or antennas for receiving and transmitting. The modulator is that part of the transponder that impresses information on the transmitted signal. A "transceiver" may be a component of a transponder responsible for transmitting and receiving signals, usually independent of one another.

Note that in the example of FIG. 3A, rectifier 109, modulator 110 and antenna 117, together act as a transponder. Rectifier 109 and modulator 110 communicate with interrogator 102 through antenna 117 and contain circuitry capable of carrying out this function. This design is specific to systems employing electromagnetic radiation of an appropriate frequency (e.g., microwave or RF) as the wireless carrier. Other transponder designs are appropriate for other wireless carriers and signals. For example, transponders may be designed for use with acoustic, optical, IR, or electromagnetic sources that are inductively or capacitively coupled. Note that the interrogator (or other probing device) may employ a multi-band or multi-frequency source having one frequency to supply power and a second frequency for interrogation, for example.

The transponder receives a wireless probe signal from an interrogator and that signal may include sufficient power to allow its transmission of the device's identifier and sensor reading back to the interrogator. The transponder is coupled to the identification memory and sensor in a manner giving it access to the identification and sensor reading during probing.

The system 100 of FIG. 3A assumes that the wireless communication takes place via electromagnetic radiation of appropriate frequency. Thus, an antenna is used. Generally, however, the interrogator and recording device may be designed to allow any suitable probe signal or carrier (not just RF or other electromagnetic radiation). The carrier should allow the device to be probed from a substantial distance and over a wide area. This may include penetration of the signal through portions of a structure. In some cases, it should also be able to power the transmission of data from the sensing device to the interrogator. The carrier should also provide sufficient bandwidth to transfer the desired information in a timely manner. Additionally, the modulated carrier may also be sufficiently unique, in terms of frequency or time synchronization, or coding, such that it is distinguishable from the signal provided by nearby sensor devices. Generally, the carrier may be a wave or field or other intangible effector that acts over a distance through a medium (vacuum, gas, fluid, solid, etc.) between the interrogator and the sensor device. Examples of suitable carriers include RF radiation, microwave radiation, visible, ultraviolet, and infrared radiation, acoustic waves, electric fields, magnetic fields, and the like. If the system employs RF radiation, the frequency preferably ranges between 100 kHz and 5800 MHz and is provided at a power of a few Watts. In a specific embodiment, the interrogator may operate at an approved frequency at or near that used for an available RFID device; e.g., near 125 kHz in one case and about 13 MHz in another case. Microwave radiation provides another preferred carrier. Generally, it provides the same functionality as RF radiation, but at larger read ranges. Typically, any approved or regulated band such as the ISM bands at 945 MHz, 5.8 GHz and 2.45 GHz may be used.

In one embodiment, sensor device 104a includes a memory component that allows for recording one or more events detected by the sensor 116. The event information is then subsequently provided to interrogator 102 via the wireless response. In one embodiment of the present invention, sensors and memory components capable of recording an event are incorporated in a microchip, either externally or internally, and may act to change the coded baseband signal directly. This advantageously allows the state change is expressed as a unique code (rather than a subtle change) that can be easily read by the interrogator.

In a simple form, the physical or chemical event is recorded by changing a "1" to a "0" or vice versa. The information recorded (whether a single bit, multiple bits, or some other information) when the event occurs can be used in two ways. First, it can be used "directly" by appending to the RFID code such that the reader obtains ID data followed by sensor data. Second, it can be used "indirectly" by selecting one of two codes; that is a particular recording device #137 could respond with code #137a if the device is normal and code #137b if the device experienced the event under consideration. From a communications theory point of view, these two codes may be orthogonal or nearly orthogonal so that the reader has a very high probability of distinguishing between a normal device and a transformed device.

In another embodiment, a silicon-based microelectromechanical system (MEMS) may be employed. Such MEMS are seeing increased usage as sensor and actuator systems in a variety of industries. MEMS are small devices integrated onto a microchip that may serve as pressure sensors, accelerometers, strain gauges, electrostatic actuators, microswitches, torsional mirrors, etc. These functions result from various MEMs structures and properties such as capacitance, temperature-dependent semiconductor activity, electrostatics, Hall effect, magnetostriction, piezoelectric effects, piezoresistance effects, etc. For example, a pressure sensor can be implemented in a MEM device in conjunction with a switch. At the over-limit condition, the deflection of a membrane could be used to close a circuit, thus discharging energy or recording the event. Exemplary MEMs temperature sensors include infrared detectors and thermocouples.

The memory component may be "unidirectional" with respect to the one or more events such that once an event has occurred, and the memory component has been altered, regressions of the event are unable to revert the memory component to a state used before the event. For example, if the event is surpassing a resistance threshold of a metllalic item being monitored, and the memory component converts from a first state to a second state as a result of surpassing the resistance threshold, resistances dropping below the resistance threshold will not revert the memory component to the first state. In many cases, the sensor and parameter being sensed are unable to drive the memory component back to a state used before the event.

Note that a single structure or mechanism can serve as two or more of components in sensor device 104. For example, a resonant electrical circuit can serve as both modulator 110 and antenna 117. Further, a single circuit can serve as both the memory described above and some or all of the transponder. For example, some sensor devices use backscatter modulation to respond to the interrogator. One way to accomplish this backscatter modulation is to vary the load impedance of a resonant circuit. The circuit that performs this function (of varying the impedance) may be described as modulator and the memory component that allows for recording one or more events.

In one embodiment of operation of system 100, transceiver 107 illuminates sensor devices 104 with a short RF pulse. For sensor device 104a, antenna 117 receives the RF signal and rectifies the signal to obtain DC power using rectifier 109. The rectified power is used to power sensor 116, which makes a measurement of the current parameter status or status. Logic 114 also receives power for rectifier 109, reads memory for the sensor device ID 112a, reads any sensor 116 data or reads data in a memory component used to store an event, and provides a digital signal to modulator 110. Modulator 110 modulates antenna 117 backscatter in response to the interrogation signal from interrogator 102. The antenna 108 and RF transceiver 107 of interrogator 102 obtains the response signal from sensor device 104a. The response signal includes ID and sensor data from sensor device 104a, and reports the ID and sensor data to computer 106. Computer 106 associates with a database and updates information for sensor 104 in the database. In some cases, software within computer 106 notes registered bridge health and signals the need for further inspection, if necessary.

Sensor devices of this invention typically include an identification (ID). Generally, a wireless probe of the sensor device should return a value or other indicator provided by the ID. That value preferably uniquely identifies the particular device providing the response. This allows it to be distinguished from a number or other devices as would be encountered in an array of devices on a system. In one embodiment, identifier tags are employed. The identifier tags are small devices that contain an identification code that can be read remotely using the interrogator. In the case of an array of sensors, the idea is to sense one or more parameters of interest at one or more locations, such as various levels of chemical concentration at graduating depths in a concrete structure, and then read sensor data out along with the device's identification code.

The ID code and digital response of device 104 also provides a means of automatically logging data entry corresponding to the status of each sensor device. This may also include logging the corresponding location in the structure. In some cases, the position and depth of each device 104 in a structure may be deduced from the amplitude and phase variations of the communicated signal. These quantities vary with depth, material permittivity and permeability, moisture content, and proximity of re-bar, if any. The present invention may thus also include algorithms that determine the depth and position of device 104 within a structure such as the depth and position of device in concrete as illustrated in FIGS. 1 and 2.

Various types of identification are known in the art and may be used with this invention. Examples of identification include microchips storing the ID code (e.g., an EPROM), magnetic sensor devices, electrical circuits providing a plurality of resonant circuits, and the like. In some cases, the identification does not include a unique number but includes other information that may distinguish a device from other similar devices. By way of example, the device's known location may be used to distinguish it from other devices.

Wireless ID tags are commercially well known and there exists numerous manufacturers that currently offer a wide selection of RFID tags. These tags are either passive (typically operating near 125 kHz) or active (often operating near 2.45 GHz). Major manufacturers include Texas Instruments of Dallas, Tex., Micron Communications of Boise, Id., and Motorola of San Jose, Calif. Commercially available RF technology is suitable for use in many designs described herein.

Because applications in which the sensor device 104 are implemented may vary considerably and may include environmentally prohibitive conditions, specific features of device 104 may be governed by a particular application. For example, in a roadway health monitoring system, all components of the sensor device 104a would be expected to survive temperatures that the road is exposed to. In various regions of the United States, bridge temperatures vary from −20 degrees Celsius to 40 degrees Celsius.

Figures 3B, 3C:
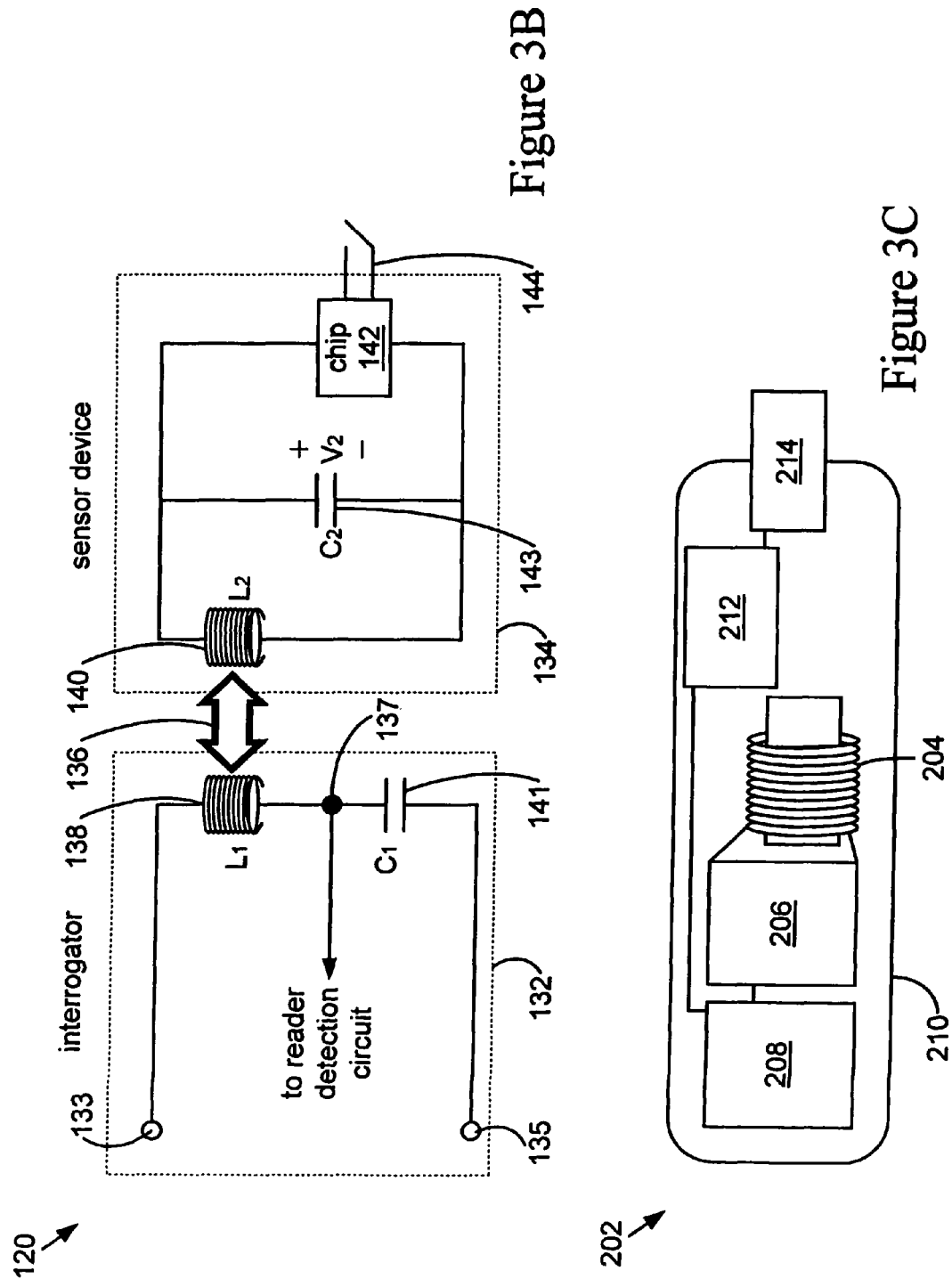
FIG. 3B illustrates an electrical equivalent circuit for the system schematized in FIG. 3A in accordance with a specific embodiment of the present invention.
FIG. 3C illustrates typical components of a commercial low-frequency RFID sensor device in accordance with another embodiment of the present invention.

FIG. 3B illustrates an electrical equivalent circuit 120 for the system schematized in FIG. 3A in accordance with a specific embodiment of the present invention. Inductive coupling between interrogator 132 and sensor device 134 is represented in this circuit by mutual inductance 136.

Interrogator 132 includes leads 133 and 135 from an oscillator or similar circuitry that provide current at a particular frequency for antenna 138. In a specific embodiment, antenna 138 operates at 125 kHz. Leads 133 and 137 allow reader data detection circuitry to measure any responses received by antenna 138. Inductance 136 in the reader circuit 132 is series resonated with capacitor 141 to maximize the current through the reader antenna 138. This technique maximizes the magnetic field generated at the antenna 140 of sensor device 134.

In contrast, the inductance in sensor device circuit 134 is parallel resonated with capacitor 143 to maximize the voltage across antenna 140. This technique maximizes the peak RF voltage that is rectified to power producing microchip 142. The voltage produced by microchip 142 is provided to an output power supply switch 144, a sensor, or other components of device 134.

In one embodiment, the design of antenna coils 138 and 140 is driven by a desire to maximize mutual inductance between interrogator 132 in sensor device 134. The mutual inductance between two coils may be approximated by:

$$M_{21} = [\mu_{eff}\mu_0 \pi R^2{}_2 R^2{}_1 N_1 N_2]/[2(D^2 + R^2{}_1)^{3/2}$$

although this mutual inductance depends on effective permeability, $\mu_{eff}\mu_0$, of the tag coil core and the distance between coils, D, noteworthy intrinsic coil parameters are its radius, $R_1$, and its number of turns, $N_1$. Thus, in one embodiment, coil 140 diameter and number of turns are as large as possible without exceeding space limitations of device 134 or causing coil 140 to be self resonant at the operating frequency. In addition, self inductance of device 134 should not be so large that resonating capacitor 143 is too small. In a specific embodiment, resonating capacitor 134 is at least 10 pF.

Often the identifier is closely coupled to the transponder. For example, FIG. 3C illustrates typical components of a commercial low-frequency "rice-grain" RFID sensor device 202 in accordance with another embodiment of the present invention. Sensor device 202 may include a ferrite-rod inductor 204 including a coil antenna, resonating capacitor 206, and silicon microchip 208. In one embodiment, the coil antenna is constructed using an air core and a ferrite rod. RF energy is inductively coupled to the RFID coil. When sufficient voltage is available, the microchip 208 is able to produce a sufficient rectified DC voltage to power the microchip. When powered, microchip 208 returns its ID and by modulating the impedance of the resonating coil. Suitable modulation schemes include ASK, PSK, and FSK for example. The components are conventionally connected together using bonding wire or rigid metal rails. The entire RFID, together with a sensor 214 and a memory component 212, may be encapsulated in cement 210 or another suitable environmental protection material. This particular device is about the size of a grain of rice, but other shapes are available commercially.

Figure 3D:
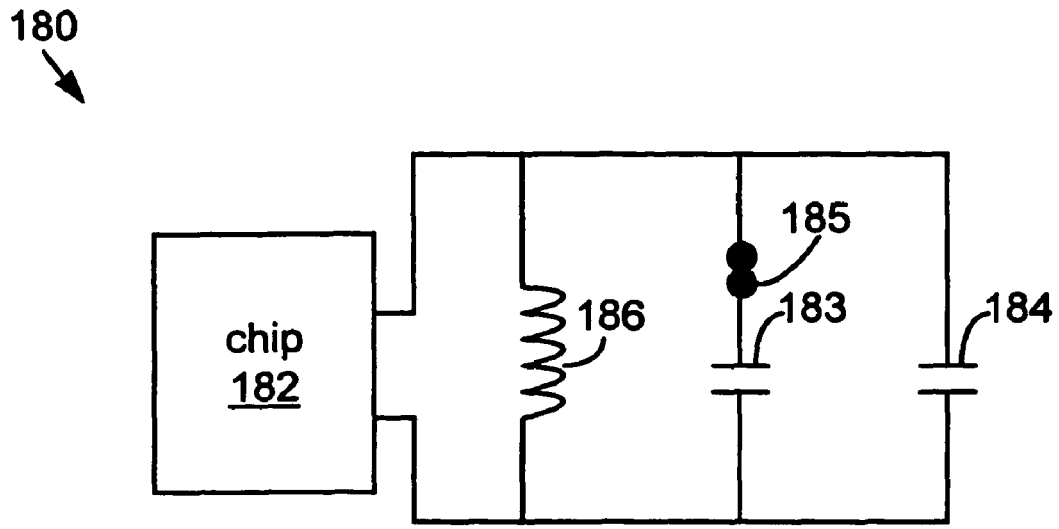
FIG. 3D illustrates a sensor device that communicates information related to a parameter being monitored based on a frequency shift in accordance with one embodiment of the present invention.
Figure 3E:
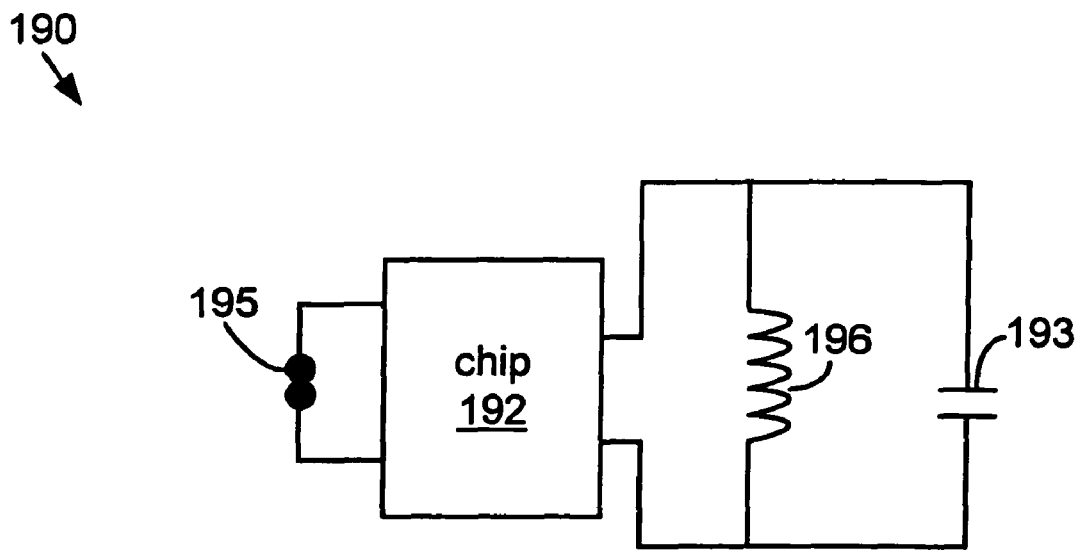
FIG. 3E illustrates a sensor device that communicates information related to a parameter being monitored based on bit stream inversion in accordance with one embodiment of the present invention.

A sensor device of the present invention may respond with a quantitative indication of the parameter or with a specific state of the sensor. For example, a fuse may be used to measure corrosion of a surrogate thin wire that parallels corrosion of a metal element in a structure. If the wire corrodes and breaks, the wire failure event is detected by a state change of the fuse. The failure event may then be used to signal significant corrosion in the metal. FIGS. 3D and 3E illustrate two concepts for determining a sensor state from ID data received from a sensor device in accordance with two embodiments of the present invention.

The sensor device 180 of FIG. 3D communicates information related to a parameter being monitored based on a frequency shift. System 180 comprises a microchip 182, resonating capacitors 183 and 184, fuse 185, and antenna 186. Resonating capacitors 183 and 184 are disposed in parallel and used to establish resonant frequency sufficiently far apart from each other. If fuse 185 is closed, the sensor device achieves its maximum response at one frequency. When fuse 185 is open, its maximum response is a different frequency. This allows sensor state system 180 to provide binary feedback pertaining to whether a particular threshold for a parameter being measured has been met. In a specific embodiment, microchip 182 is a MCRF200 microchip as provided by Microchip Technology, Inc. of Chandler, Ariz.

The sensor device 190 of FIG. 3E communicates information related to a parameter being monitored based on bit stream inversion. System 190 comprises a microchip 192, capacitor 194, fuse 195, and antenna 196, all in parallel. System 190 provides binary feedback pertaining to whether a particular threshold has been met according to an inversion of the ID code of microchip 192 when fuse 195 is open. In this case, an interrogator probing the sensor distinguishes the difference between the two codes produced from microchip 192. System 190 will also work if the fuse/switch is replaced by a suitable voltage level change, such as the output from a comparator. In a specific embodiment, microchip 192 is a MCRF202 microchip as provided by Microchip Technology, Inc. of Chandler, Ariz.

Figure 3F:
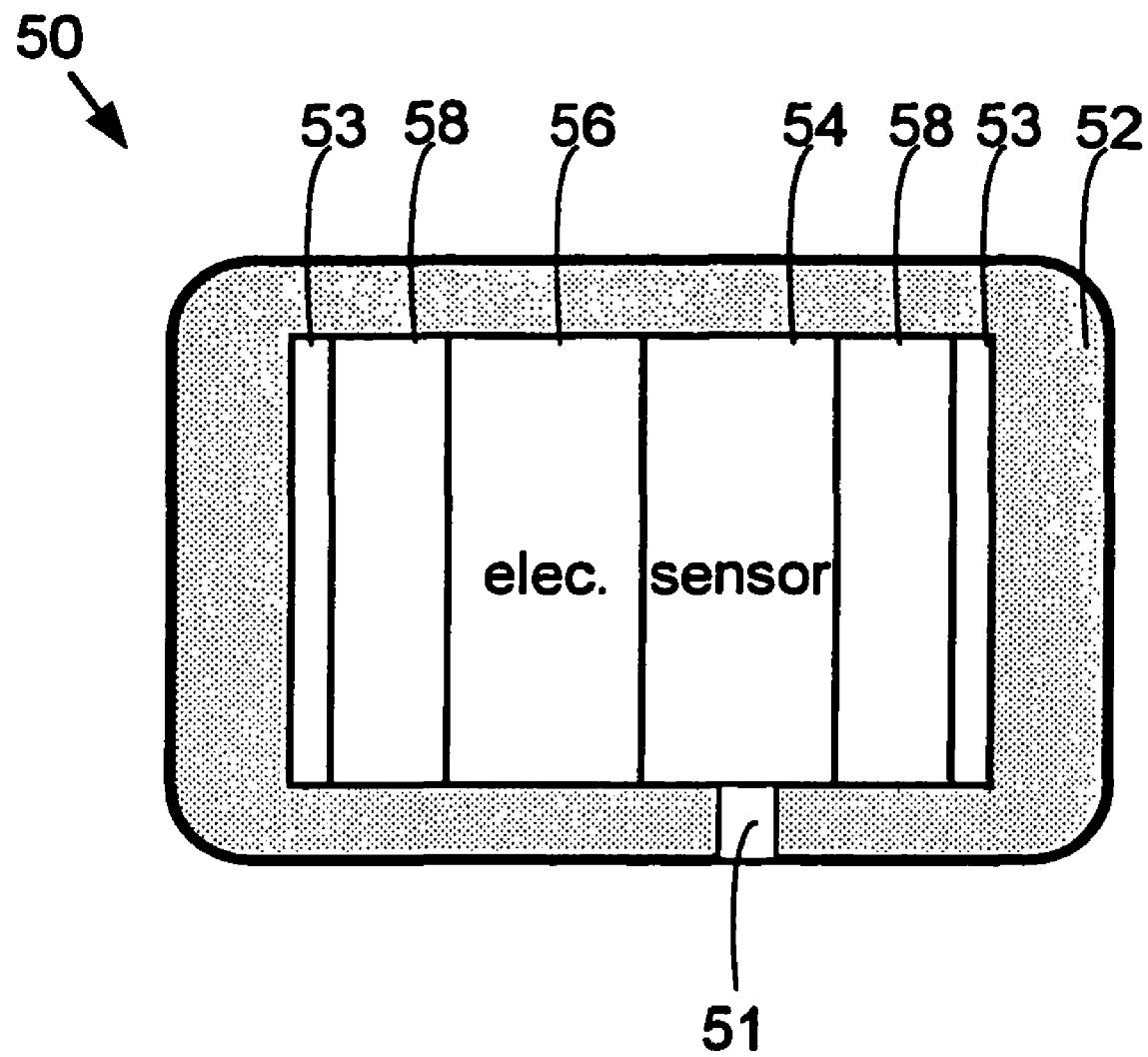
FIG. 3F illustrates a simplified cross-section view of a sensor device in accordance with another embodiment of the present invention.

In one embodiment, a sensor device of the present invention comprises an RFID technology and a sensor encapsulated in a pebble-sized enclosure and embedded into the concrete structure. FIG. 3F illustrates a simplified cross-section view of device 50 in accordance with another embodiment of the present invention. Device 50 includes an encapsulation 52 that defines an interior 53. Within interior 53 is sensor 54, electronics 56, ferrite coil 58, and coil windings 59. In a specific embodiment, device 50 of FIG. 3F is cylindrical and has a diameter in the range of about ½ inch to about 2 inches and a height of about ½ inch to about 2 inches. In another specific embodiment, device 50 is characterized by a maximum dimension less than about 3 inches.

Encapsulation 52 seals internal components of device 50 from the surrounding structure and environment. Encapsulation 52 also comprises an inlet port 51 that allows intimate interface to the surrounding structure. In one embodiment, port 51 is permeable to chloride ions and allows diffusion of chloride through port 51 for reception by sensor 54. Port 51 is comprised of a material corresponding to the parameter being monitored and specific application. For detection of chloride ion presence in a particular concrete, port 51 may comprise any material that allows diffusion of chloride ions such as concrete or any other permeable cementitous material.

As will be described in more detail below, sensor 54 detects a parameter, such as a parameter associated with the health of a structure that device 50 is embedded within. Sensor 54 may detect a simple binary threshold level corresponding to a parameter of interest, or may generate an electric potential dependent on a parameter being monitored, e.g., the concentration of chloride ions received at sensing elements.

Electronics 56 may include one or more of the following structures: a) processing logic and electronics that convert a response generated by sensor 54 into a suitable response signal for transmission from device 50, b) receiving electronics that rectify an incoming probe signal from an interrogator to power one or more components of device 50, c) measurement correction electronics that adapt measurements provided by sensor 54 and/or correct for any environmental conditions, if necessary, and d) identification electronics that allow device 50 to be uniquely identified from an array of similar devices 50. Electronics 56 may also include interface electronics between processing logic in the device and the sensor. The interface electronics will depend on the sensing components. As shown with respect to the circuit diagram of FIG. 4D for example, interface electronics between a chloride sensor 362 and microchip 364 include operational amplifier 368 and analog to digital converter 370.

In one embodiment, device 50 may be realized by integrating a sensor with a passive commercial radio frequency identification (RFID) microchip. Such a microchip is also commonly referred to as a 'tag' because of its widespread use in inventory control. Commercially available RFID technology may then be integrated with an array of devices 50 and interrogator designed to communicate with each device 50. In one embodiment, each device 50 comprises and RFID microchip such as the MCRF200 or MCRF202 as provided by Microchip Technology, Inc. of Chandler, Ariz.

In one embodiment, device 50 is designed for long-term inspection applications and one or more components of device 50 do not require continual power for operation. In this case, energy may be supplied to the sensor device using a wireless illumination, such as radio frequency or microwave frequency illumination. Some sensor devices of the present invention require from about 5 microwatts to about 50 microwatts of power as supplied by an interrogator, and may consume energy on the order of a few hundred nanojoules. Other sensor devices of the present invention require from about 10 microwatts to about 25 microwatts of power as supplied by an interrogator. Illumination of a chloride sensor as described with respect to FIG. 4C for example may result in available energy in the order of a few tens of microjoules.

In one embodiment, a sensor device of the present invention is passive. As the term is used herein, passive refers to the notion that the device, or any of its components, do not rely on a local continual power source, e.g., such as a battery, included in the device. As described above, power for responding to a wireless interrogation may be temporarily achieved using a wireless interrogation. Passive sensor devices that derive their power from RF illumination eliminate the need for battery power and battery maintenance. In one embodiment, a passive sensor included in an embedded sensor device of the present does not make a sensor reading until triggered by RF illumination.

The ability for devices of the present invention to operate without dedicated or internal power allows embedded sensor devices to sense and report data for extended periods up to, in some cases, the lifetime of a structure. For example, passive sensor devices of the present invention are well-suited for long-term inspection applications such as inspection of chloride ingress into road structures. Bridge design life goals are about 75-100 years. Because sensor devices of the present invention do not use batteries or limited life power supplies, monitoring of bridges and extended longevity structures is indeed possible.

Alternatively, concrete monitoring using devices of the present invention may include passive sensors that perform long-term and passive monitoring of moisture, pH, chloride, and other environmental and structural parameters of interest. Passive sensing also allows devices as described herein to transpond data either in real-time or transponder threshold events or exposures recorded in the past. It is contemplated that not all sensor devices of the present invention need be passive and some may include an internal power supply such as a battery.

In one embodiment, sensor devices of this invention include some form of recording mechanism coupled to the sensor. The memory device may record a physical or chemical event when the sensor provides an indication that the event has occurred. "Recording" usually means that the mechanism has changed. As discussed with respect to FIG. 3E for example, the recording mechanism changes the device's resonance frequency. For the device of FIG. 3E, a digital value in a memory location changes. The sensor device may be designed such that the state change does not spontaneously reverse. Thus, when the physical or chemical event triggers a change from state 1 to state 2, the recording mechanism remains in state 2 even after the physical or chemical event ceases or reverses back to state 1. Alternatively, the sensor device may be designed such that the state change reverses with a change of the parameter back to state 1.

The sensor device may also be designed such that the state change is reversible. This is particularly useful for monitoring reversible and effective extraction of chloride ions from roadways and bridge decks. Remediation strategies are available to extract chloride out of bridge decks, such as electrochemical extraction. Thus, sensor devices described herein may allow a chloride sensor to be restored to an initial state from an over limit state, thereby indicating that a remediation treatment has been effective.

When used, the recording mechanism should cause a sufficient change in the operation of the sensor device to be detectable by the chosen interrogation means. In the case of a resonant circuit, for example, the frequency shift recording the event needs to be measurable. Generally, the recording resonant circuit needs to change frequency by an amount greater than the width of the resonance (quality factor Q). Examples of recording mechanisms include electrical circuits, electromechanical circuits, mechanical latching mechanisms, programmable integrated circuits such as EPROMs, fusible links, magnetic circuits, acoustic circuits, optical/IR circuits, and the like.

In some embodiments, a memory component includes multiple recording mechanisms, all able to store and record different physical or chemical parameter levels or events. The different physical levels or events may all pertain to the same parameter such as various chemical concentrations. For example, a chemical concentration detection system may include three separate recording components and/or sensors, each configured to record a separate threshold chemical concentration relevant to monitoring chloride ingress into a bridge deck.

Some identifier tag/interrogation systems are designed to be polled one at a time (serially), while other interrogators are able to poll multiple tags simultaneously. In practice, more than one sensor device 50 may be an interrogator's interrogation field at a time. To prevent collision of overlapping response signals, techniques may be implemented to distinguish between different but adjacent, sensor devices. Communications techniques typically make use of anti-collision and arbitration procedures that control the time when a tag responds to a probe. Different RFID manufacturers implement different anticollision algorithms. One approach is to have each sensor device transmit at a random time slot and have the interrogator search different time slots and reject multiple readings of the same tag.

4. Exemplary Sensor Designs

Specific sensors that may be used in some embodiments of this invention include sensors that detect or measure chemical or biochemical species, temperature sensors, electrochemical cells that measure the presence or level of an ion, pressure sensors, flow sensors, stress/strain sensors, accelerometers, dielectric sensors, conductivity sensors, shock sensors, vibration sensors, position sensors, sensors that detect thermal exposure, optical exposure, x-ray exposure, microwave exposure, pollutants, particle size, alignment, and the like.

Most any type of sensor may be used with this invention, so long as it meets the functional requirements. Sensors may be classified based upon the parameters that they sense and the transduction mechanisms they employ. Very many sensor types are known and used for different applications. Many examples of things to be sensed and sensing mechanisms are described by Julian W. Gardner in "Microsensors: Principles and Applications," John Wiley, 1994 (incorporated herein by reference in its entirety and for all purposes). Among the listed items are (1) thermal sensors: temperature, heat, heat flow, entropy, heat capacity; radiation sensors: gamma rays, X-rays, UV, visible, IR, microwaves, radio waves; mechanical sensors: displacement, velocity, acceleration, force, torque, pressure, mass, flow, acoustic wavelength, amplitude; magnetic sensors: magnetic field, flux, magnetic moment, magnetization, magnetic permeability; chemical sensors: humidity, pH level and ions, concentration of gases, vapors and odors, toxic and flammable materials, pollutants; electrical sensors: charge, current, voltage, resistance, conductance, capacitance, inductance, dielectric permittivity, polarization, frequency, and the like.

A transduction mechanism is usually used to convert the sensed parameter or stored event into an electrical signal. Suitable transduction examples include electrochemical, conductometric (changes in resistance or conductivity), potentiometric, capacitive, amperometric, calorimetric, optical, resonant, fluorescent, piezo-electric, optoelectric, magnetooptic, surface-acoustic wave, magnetoresistive, superconductive, and other effects.

Conventionally, most sensors are stand-alone, directly powered devices that provide continual measurements of the quantity being sensed. These devices often require their own battery or wiring to a central power source. For many applications of this invention, such conventional active sensors are not suitable because power requirement limits operational lifetime, or are embedded in an inaccessible location of a structure that denies wired power. Many applications require parameter detection at highly infrequent intervals in the range of several readings per year. Thus, many sensors of the present invention are passive and receive energy from the parameter being sensed or the environment that the sensor is implemented in.

FIG. 4A illustrates a simplified cross-section view of a chloride ion sensor device 140 in accordance with one embodiment of the present invention. Device 140 is embedded and surrounded by concrete 145. As shown in FIG. 4A, device 140 comprises a chloride ion sensor 142, threshold detector 144, antenna 146, temperature sensor 148, encapsulation 149 and microchip 147. Encapsulation 149 seals the components of device 140 from the exterior of device 140 and includes port 143. Port 143 allows chloride ions to pass between the exterior 145 of device 140 and sensor 142.

Chloride ion sensor 142 detects the presence of chloride ions. In one embodiment, chloride ion sensor 142 converts a chloride ion level, such as chloride ion concentration, to an electrical output such as voltage. As shown, chloride ion sensor 142 detects a level of chloride ions that pass through port 143.

Threshold detector 144 compares one or more particular levels of output from sensor 142 with a predetermined threshold for an application. If sensor 142 outputs a voltage, then threshold detector 144 may be a comparator that compares the voltage from sensor 142 with a predetermined voltage. The predetermined threshold voltages correspond to one or more particular chloride ion concentration levels of interest. Typically, the particular levels detected by threshold detector 144 are determined upon implementation of device 140. For a comparator, threshold levels may easily be established and modified using predetermined voltages on the comparator. Threshold detector 144 may also include a memory component such as a latch that changes in some way when a threshold has been reached.

Microchip 147 responds to an interrogation signal as received by antennae 146 and includes instructions, circuitry and other facilities for this purpose. Microchip 147 may comprise a logic device, microprocessor, and/or one or more conventional processors. Chip 147 also prepares a signal to be transmitted from sensor device 140 in response to an interrogation signal. This may include modulating a reading or response provided by chloride ion sensor 142 or threshold detector 144, for example. Chip 147 may include a rectifying facilities that rectify an incoming probe to power one or more components of device 140 and identification that allows device 140 to be uniquely identified from an array of similar devices. In addition, microchip 147 may also include a DC power outlet that allows collected power to be distributed to various components in device 140.

Sensor device 140 also includes measurement correction electronics that adapt measurements provided by sensor 142 and/or correct for any environmental variability that may affect sensor performance, if necessary. For example, temperature sensor 148 detects the temperature of device 140, which is usually the same as concrete surrounding device 140. Measurement correction electronics coupled to temperature sensor 148 convert output of temperature sensor 148 to appropriate modification of the signal provided by sensor 142, threshold detector 144, or microchip 147. Temperature sensor 148 is passive and receives heat energy from in concrete 145.

Figure 4B:
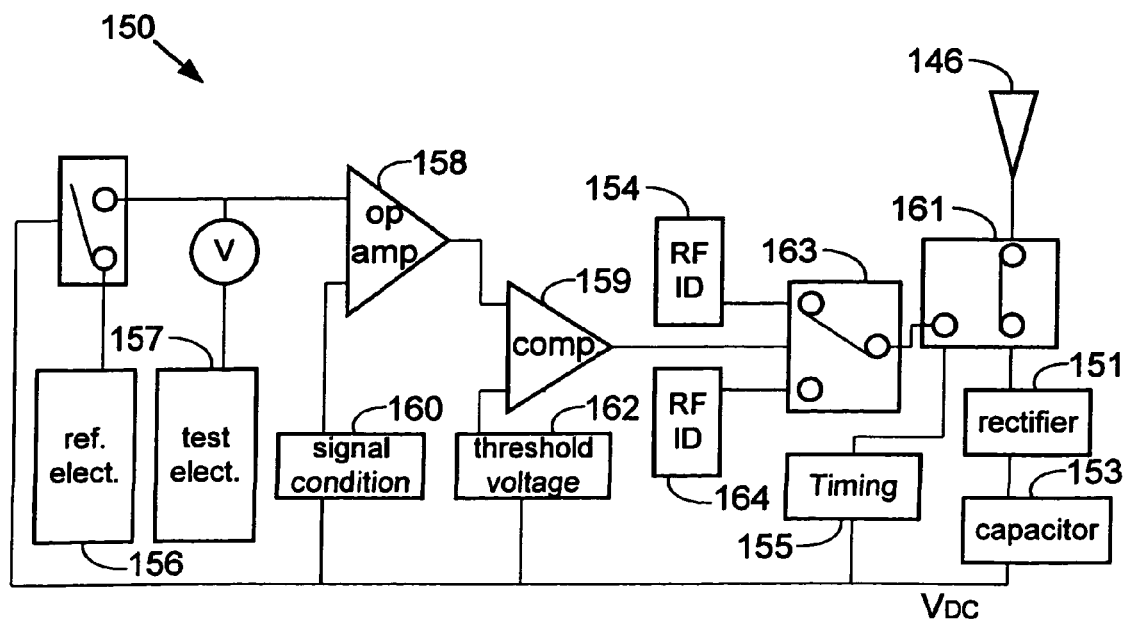
FIG. 4B shows an exemplary circuit diagram corresponding to the chloride ion sensor device of FIG. 4A.

FIG. 4B shows an exemplary circuit diagram 150 corresponding to the chloride ion sensor device 140 of FIG. 4A. As shown, sensor device 140 includes micropower circuitry including operational amplifiers and comparators are used to determine whether chloride concentrations have reached a predetermined threshold.

Starting in the upper right hand side of circuit diagram 150, antenna 146 receives RF energy from an interrogator that probes device 140. Initially, antenna 146 is connected to a DC rectifier 151 via switch 161. DC rectifier 151 provides energy to the electronics in circuit diagram 150. Capacitor 153 stores electrical energy collected by antenna 146 and provided by DC rectifier 151, and has an outlet that provides the energy at $V_{DC}$. Timing circuitry 155 coordinates components within circuit diagram 150 based on reception of a signal at antennae 146.

As shown, reference electrode 156 and test electrode 157 are included in sensor 142 and quantify the amount of an ion that they are subjected to in. Electrodes 156 and 157 output a voltage relative to the amount of the ion. Operational amplifier 158 converts the voltage difference produced by the electrodes 156 and 157 to a level suitable for comparison by comparator 159. A signal conditioner 160 may alter the output based on the temperature of concrete 145 sensed by temperature sensor 148 of FIG. 4A.

Threshold voltage 162 produces a voltage that corresponds to a threshold chloride ion concentration of interest. Comparator 159 compares the output of operational amplifier 158 with threshold voltage 162. A logical LO output from comparator 159 indicates that chloride concentrations received by sensor 142 are below the threshold and within acceptable ranges. In this case, and RFID 154 is energized at the appropriate time interval to allow the sensor to stabilize. A logical HI from comparator 159 indicates that chloride concentration is above the predetermined threshold. In this case, RFID 164 is selected by switch 163, transponding a different ID code from device 140 to an interrogator. In this manner, two separate identification numbers are produced from device 140 based on the amount of chloride detected. Alternatively, comparator 159 output may be used to modify the response of a single RFID, thereby simplifying circuit 150.

In general, a variety of sensors may be used in the wireless devices of this invention. The sensor chosen for a particular application should be able to detect the physical or chemical parameter or event under consideration. Thus, the sensor should detect a change in the parameter or parameters associated with the one or more physical and/or chemical events. Further, the sensor should have a dynamic range that covers the physical and chemical events in question. The sensor should also be able to withstand the operating conditions to which it will be exposed and fit within good design practices including reliability, accuracy, size, weight, safety, and compatibility with other components and the application. In one embodiment, an electrochemical cell is employed to detect levels of a chemical species in concrete.

Figure 4C:
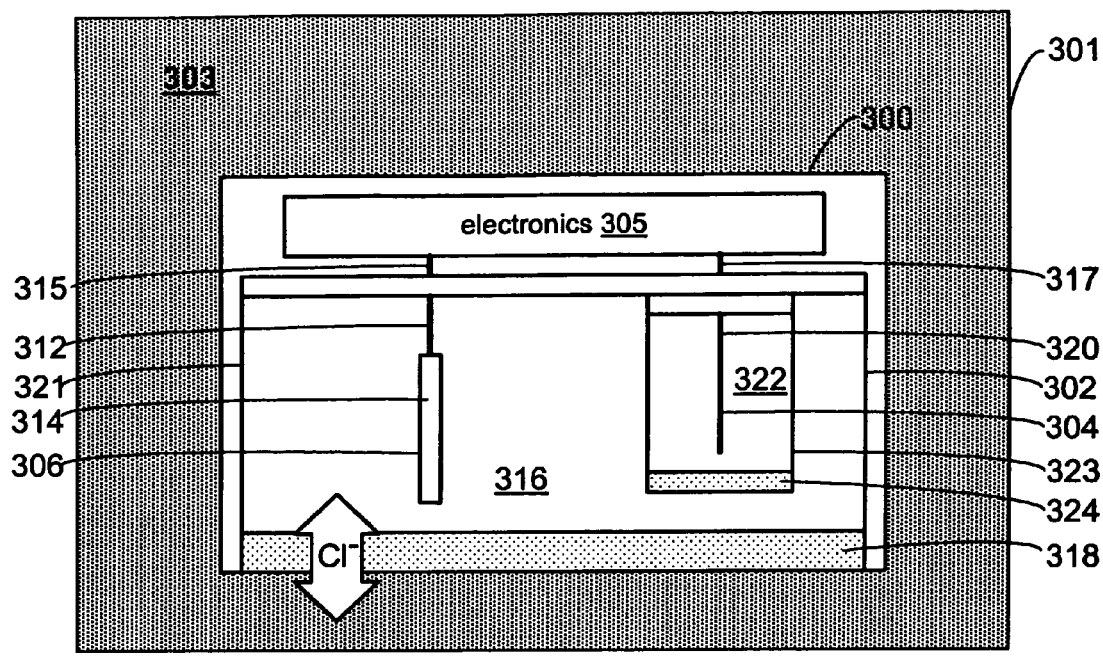
FIG. 4C illustrates an electrochemical cell sensor in accordance with one embodiment of the present invention.

FIG. 4C illustrates an electrochemical cell sensor device 300 in accordance with one embodiment of the present invention. Electrochemical cell sensor device 300 is embedded in a structure 301 comprising concrete 303 or any other cementitious material. Electrochemical cell sensor device 300 measures the concentration level of chloride ions in concrete 303 and transmits a wireless signal representative of the measurement.

Electrochemical cell 302 is an electrochemical sensor that generates an electric potential dependent on the concentration of an ion received at electrodes 304 and 306, such as chloride ions. The electrochemical cell 302 consists of two electrodes: an ion selective electrode 306 and a reference electrode 304. The output quantity of electrodes 304 and 306 is a potential difference between the two electrodes.

Ion selective electrode 306 allows the voltage difference between electrodes 304 and 306 to change with the amount of an ion received at its active element. In one embodiment, ion selective electrode 306 is an Ag/AgCl electrode that responds to the presence of chloride ions. As shown, ion selective electrode 306 includes silver (Ag) wire 312, ion selective active sensing element 314, and a lead 315 in electrical communication with one or more electrical components of sensor device 300. Silver wire 312 is coupled on one end to active sensing element 314 and to lead 315 at another end. Silver wire 312 allows electrical communication between sensing element 314 and lead 315. Active sensing element 314 comprises silver chloride and is disposed in electrolyte 316, which provides a medium for movement of chloride ions. In a specific embodiment, the AgCl is melted onto the active sensing element 314. Electrolyte 316 maintains electrical connection between ion selective electrode 306 and reference electrode 304. Electrolyte 316 is contained and sealed within an outer shell 321 and comprises a saturated solution of calcium hydroxide, or any other suitable charge carrying aqueous liquid or solution. Permeable cementitous material 318 leads to an external port of sensor device 300 and allows communication of chloride ions between concrete 303 and electrolyte 316.

Ag/AgCl is a suitable chloride sensing electrode. Hg/HgCl may also be used, but hazards associated with mercury make it undesirable for some applications. Sulfide ($S^=$) could be sensed using a $Ag/Ag_2S$ electrode, pH could be sensed using nickel/nickel oxide or iridium/iridium oxide, sulfate could be sensed using $Hg/Hg_2SO_4$, etc. Electrodes are generally chosen to be sensitive to the ions to be sensed (chloride ions in this case) and insensitive to ions that could confuse the measurement. These choices are well-known to those skilled in the art of electrochemical measurement. For example, http://www.topac.com/ISE.html lists a variety of commercially available electrodes designed to detect specific ions. Although these electrodes are not consistent with the size and geometry of many devices described herein, a sensor devices could be constructed to sense any of these quantities using the proper electrode material.

Healthy concrete has a high pH, in the order of about 12-13. As concrete matures over its lifetime, the pH decreases due to environmental effects such as carbonation. Sensor devices of the present invention are substantially insensitive to pH changes in concrete and other structures. In one embodiment, electrolyte 316 contains an excess of calcium hydroxide to maintain substantially constant pH for electrolyte 316.

Reference electrode 304 provides context for the voltage difference between electrodes 304 and 306. In one embodiment, reference electrode 304 is a copper electrode. As shown, reference electrode 304 includes copper (Cu) wire 320, electrolyte 322, permeable cementitious material 324 and lead 317 in electrical communication with one or more electrical components 305 of sensor device 300. Copper wire 320 is coupled on one end to lead 317. Electrolyte 322 is contained and sealed within a containment shell 323 and provides a medium for the storage and movement of ions provided through permeable cementitious material 324. Electrolyte 322 is saturated with copper sulphate ($CuSO_4$) and calcium hydroxide, or any other suitable charge carrying aqueous liquid or solution. In one embodiment, electrolyte 316 contains an excess of calcium hydroxide to maintain substantially constant pH for electrolyte 322.

In operation, chloride ions ($Cl^-$) penetrate inlet membrane 318 from the surrounding concrete 303. The chloride ions collect in electrolyte 316. The Ag/AgClion selective electrode 306 is reversible to chloride ions according to the Nernst equation, and hence its potential depends on the activity of chloride ions. The potential of this electrode is measured with the respect to the reference electrode. The voltage between 304 and 306 is proportional to the logarithm of the chloride concentration. The voltage between electrodes 304 and 306 changes and may be measured via a resistor included in electronics 305.

While electrochemical cell sensor device 300 has been described with respect to measuring chloride ions, ion selective electrode 306 may be configured or designed to detect the presence and concentration of any halide and is not limited to chloride ion selectivity. In addition, ion selective electrode 306 may be designed such that it is selective to any ion—particularly one that facilitates corrosion of a metal—and is not limited to halide ion selectivity.

Chloride ion sensors of the present invention, such as electrochemical cell 300 of FIG. 4C, may be configured to detect a wide range of chloride ion concentrations. In one embodiment, sensor 302 detects threshold chloride concentration in the range of about $10^{-3}$ to about $10^{-5}$ (weight percentage of cement) in an environment with the pH ranging from about 8 to about 14. In a specific embodiment, sensor 302 detects threshold chloride concentration in the range of about $10^{-4}$ (weight percentage of cement) in an environment with the pH ranging from about 9 to about 13. In another embodiment, personnel may set a threshold for chloride ion concentration greater than about 30 milliMolars, as determined by an application.

In specific embodiments, a chloride ion sensor of the present invention is configured to detect chloride ions in the range of about 10 milliMolars to about 100 milliMolars. Some sensors detect a threshold that corresponds to a corrosion initiation threshold in for a metal in concrete. One such threshold is 30 milliMolar chloride ion for reinforcing steel in Flyash concrete. Another particular corrosion initiation threshold for a metal in concrete corresponds to about 24 milliMolars (about 0.857 kg/m$^3$). Yet another particular corrosion initiation threshold for a metal in concrete corresponds to about 33 milliMolars for an admixture concrete. For some health monitoring applications, the accepted threshold value for chloride ion ingress is about 0.014% chloride ion by weight percent of cement. Obviously, sensors of the present invention may be designed to detect a wide range of chloride ion levels. One of skill in the art will appreciate that a particular chloride ion level will vary on a wide variety of factors such as the metal material composition, concrete type, etc. Other factors that may affect design parameters for a chloride sensor of the present invention include the typical chloride concentrations expected to be seen in the structure, the rate of chloride diffusion in the structure, the sensor device characteristics such as power availability, and other system constraints such as temperature and pressure of the surroundings.

Thus, electrochemical cell within sensor device 300 measures a potential difference between a reference electrode 304 and an ion selective electrode 306. Leads 315 and 317 from reference electrode 304 and ion selective electrode 306 are in electrical communication with electronics 305. Electronics 305 include memory 310 and a transponder 308. Memory 310 acts as an identification source that uniquely identifies the device, and is in electrical communication with transponder 308. Here, 'unique' is relative to other similar sensor devices 300 embedded in structure 301. In one embodiment, memory 310 also stores a second unique number for sensor device 300 that indicates when electrochemical cell 302 has detected a threshold potential level for chloride ions in concrete 303. The memory may be a stand alone digital memory source or included in a microchip that that rectifies a signal provided to transponder 308. One suitable microchip for these purposes is a MCRF202 microchip as provided by Microchip Technology, Inc. of Chandler, Ariz. When triggered by a wireless interrogation signal, the transponder transmits a wireless signal that indicates the potential difference status between electrodes 306 and 304, and includes information from memory such as a unique number for sensor device 300. Since device 300 is embedded, the signal is normally sent through a portion of concrete 303.

Electrochemical cell sensor device 300 is passive. This implies that all components in sensor device 300 do not require dedicated power stored in device 300. The electrochemical cell for example relies on a concentration gradient to provide sensing energy. Operation of passive transponders and energy capture from an incoming interrogating signal has been described above.

Figure 4D:
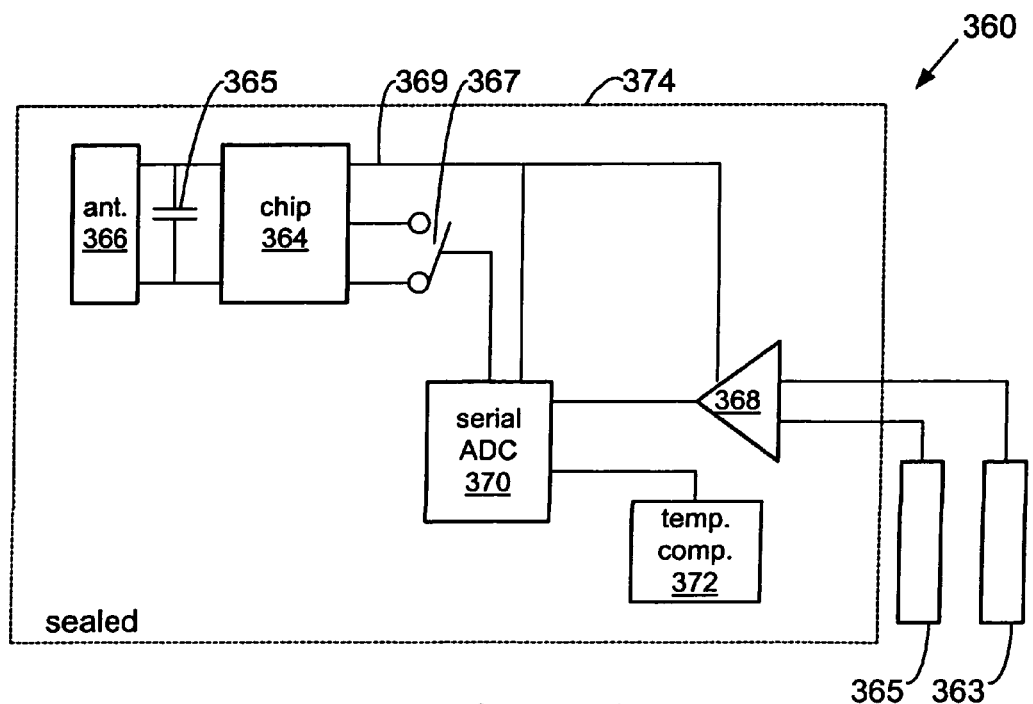
FIG. 4D illustrates a representative potentiometric threshold measurement circuit for the electrochemical cell sensor device of FIG. 4C in accordance with one embodiment of the present invention.

FIG. 4D illustrates a representative potentiometric threshold measurement circuit 360 for the electrochemical cell sensor device 300 of FIG. 4C in accordance with one embodiment of the present invention. Circuit 360 comprises electrodes 363 and 365, microchip 364, antenna 366, operational amplifier 368, serial analog to digital converter (ADC) 370, and temperature compensation circuitry 372. All the components of circuit 360 except electrodes 363 and 365 are sealed within an interior cavity of sensor device 300, as indicated by seal 374. Electrodes 363 and 365 may each be sealed in their own respective containment spaces, such as containment spaces 323 and 321 as described above.

Antenna 366 receives RF energy from an interrogator that probes circuit 360. Microchip 364 rectifies the RF energy and energizes the electronics in circuit 360. Capacitor 365 stores electrical energy collected by antenna 366. Microchip 364 has an outlet 369 that provides electrical energy. In a specific embodiment, microchip 364 produces electrical energy at 5 microamps at five volts.

Electrodes 363 and 365 quantify the amount of an ion that they are subjected to. Operational amplifier 368 converts the potential difference produced by electrodes 363 and 365 to a level suitable for comparison by serial ADC 370. Serial ADC 370 converts the analog signal provided by operational amplifier 368 to a digital signal.

In addition, serial ADC 370 includes measurement correction electronics that alter output from electrodes 363 and 365 to correct for environmental variations. Exemplary environmental variations that may be compensated for by correction electronics included in a sensor device include temperature, pH and wetness. Devices of the present invention embedded within concrete and roadways are expected to survive temperatures from about −10 degrees Celsius to about 50 degrees Celsius. These temperatures should not compromise sensor performance. Temperature compensation circuitry 372 is then included to accommodate for temperature differences in the surrounding structure. Temperature compensation circuitry 372 includes a temperature sensor that detects the temperature of concrete surrounding device 300, and outputs a signal that corresponds to the sensed temperature. Temperature compensation circuitry alters a reading provided by electrodes 363 and 365 according to temperature of device 300. Typically, the temperature of device 300 corresponds to the temperature of the ambient material that device 300 is disposed in.

ADC 370 includes comparative facilities that compare the output of operational amplifier 368 with a threshold voltage, and factor in the output from temperature compensation circuitry 372. A switch 367 is coupled to the output of ADC 370 and informs microchip 364 when the threshold has been reached. In a specific embodiment, microchip 364 is an MCRF202 as provided by Microchip Technology, Inc. of Chandler, Ariz. This chip is capable of indicating when a threshold level has been exceeded by inverting the ID code bitstream, and is able to power electronics within circuit 360.

Figure 4E:
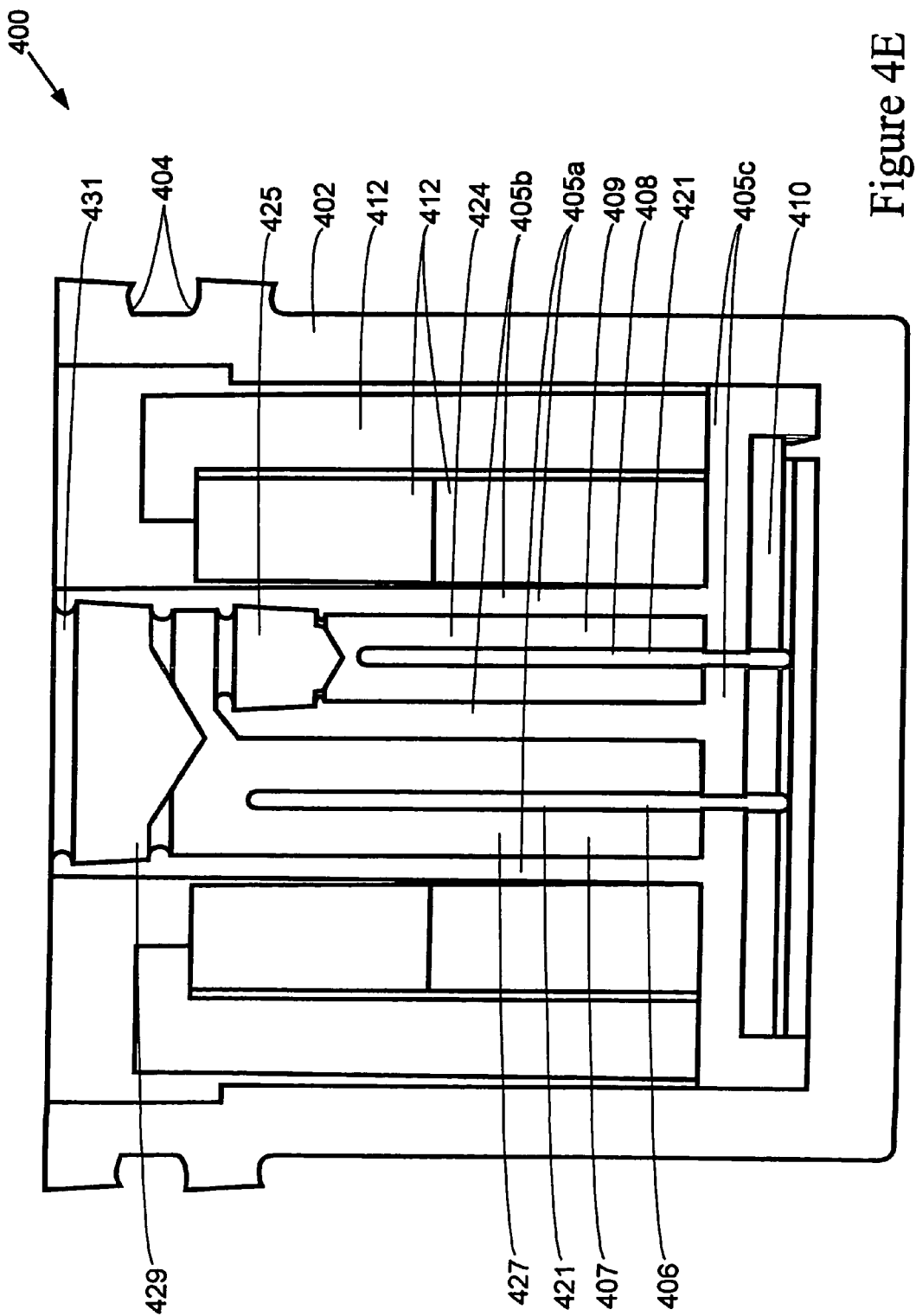
FIG. 4E illustrates a detailed arrangement for a sensor device in accordance with one embodiment of the present invention.

FIG. 4E illustrates a vertical cross section view of a vertically cylindrical sensor device 400 in accordance with one embodiment of the present invention. Sensor device 400 comprises housing 402, a transponder, two electrochemical electrodes 406 and 408 contained in separate reservoirs 407 and 409, respectively, and board 410 including a logic device.

Housing 402 provides physical protection for internal components of sensor device 400. This includes sealing the components from moisture in the ambient structure. Housing 402 includes an interface 404 that allows coupling or attachment of device 400 to rebar, tendons, or other metal elements in a structure. In a specific embodiment, housing 402 is made from molded plastic. An encapsulation comprising concrete may also be disposed around housing 402 to make the external appearance of device 400 resemble a common concrete pebble.

Sensor device 400 includes structural members for separating and containing various elements of sensor device 400. Lining 405 contributes to an aqueous seal and fluid containment for reservoirs included in device 400 and comprises cylindrical lining portions 405a and 405b. Cylindrically lining portion 405a contributes to an aqueous seal and fluid containment for reservoir 409. Disposed within reservoir 409 is cylindrical lining portion 405b, which contributes to an aqueous seal and fluid containment for reservoir 407. Cylindrical lining portions 405a and 405b are both attached to a bottom portion 405c of lining 405. Lining 405 may be made of rubber or Teflon, for example.

The transponder in sensor device 400 comprises ferrites 412, spacer 413, and wire 414. Ferrites 412 are cylindrical and surround cylindrical rubber lining portion 405b. In one embodiment, ferrites 412 comprise a low loss conductor with high magnetic permeability, such as a ceramic/metal mixture. Ferrites 412 help focus electromagnetic energy between the interrogator and sensor device. As shown, two cylindrical ferrites are used in device 400. Spacer 413 is cylindrical and surrounds ferrites 412. Spacer 413 reduces the capacitance of the coil for wire 414 such that it resonates at a higher frequency. Wire 414 is wound around spacer 413 and ferrites 412, and acts as an antennae that senses a magnetic field. The transponder in sensor device 400 is strong enough to communicate (listen and transmit) through concrete between device 400 and an associated interrogator. For example, read ranges of at least twelve inches are possible with device 400. In one embodiment, wire 414 has an outside diameter from about ½ inch to about 4 inches and between about 100 and 500 turns. In a specific embodiment, wire 414 is comprised of 42 gauge copper and has an outside diameter about 1¼ inches and about 300 turns while ferrites 412 is a 1¼ inch outside diameter ferrite torrid as provided by Fair-Rite Products, Corp., Wallkill, N.Y.

Device 400 includes an electrochemical sensor that generates an electric potential dependent on the concentration of chloride ions received by the device. Electrodes 406 and 408 comprise an ion selective electrode 406 and a reference electrode 408.

Reference electrode 408 provides context for the voltage difference between electrodes 406 and 408. As shown, reference electrode 408 comprises copper lead 421 disposed in an electrolyte 424 saturated with copper sulfate. Electrolyte 424 may comprise any suitable solution suitable for carrying charge and is not limited to a copper sulfate solution. Electrolyte 424 is contained within in reservoir 407 and provides a medium for the movement of ions provided through cementitious membrane or plug 425. The volume of reservoir 407 is defined by rubber lining 405b and the lower surface of cementitious membrane 425. Cementitious membrane 425 is permeable to silver ions and allows communication of silver ions between electrolyte 427 and electrolyte 424.

Ion selective electrode 406 allows the voltage difference between electrodes 406 and 408 to change with the amount of chloride ions received at its active element. Ion selective electrode 406 comprises a silver chloride (AgCl) lead 421 that responds to the presence of chloride ions as the electrode is reversible to chloride ions. Lead 421 is disposed in an electrolyte 427 comprising calcium hydroxide in water. Electrolyte 427 may comprise any suitable solution suitable for carrying charge and is not limited to calcium hydroxide in water. Electrolyte 427 is contained within in reservoir 409 and provides a medium for the movement of chloride ions provided through cementitious membrane 425 and a medium for the movement of silver ions emitted from lead 421. One or more chemicals may be added to electrolyte 427 to enhance ion conductivity. For example, copper sulphate added as a paste in reservoir 409 may be suitable to enhance ion conductivity. The volume of reservoir 407 is defined by rubber lining 405b and the lower surface of cementitious membrane or plug 429. Cementitious membrane 429 is permeable to chloride ions and allows communication of chloride ions between concrete the external environment and electrolyte 427.

As shown, membrane 429 is blocked by environment interface membrane 431, which controls inlet and outlet of chemicals and molecules for device 400. Membrane 431 permits selective ion inlet and prevents moisture loss from device 400. Device 400 is often implemented in a bridge where chloride ions travel faster when the bridge is wet. Since the bridge will subsequently dry, obtaining chloride ions and sensor measurement is preferably performed during wet conditions. The device then provides data based on chloride penetration when the bridge is wet and ion travel is greatest, not at the time of interrogation when the bridge is dry. In a specific embodiment, membrane 431 comprises a cementitious material (e.g., tile grout).

Electrodes 406 and 408 pass through rubber lining 405 and are in electrical communication with board 410, e.g., via a solder connection. Rubber lining portion 405c seals the passage of each electrodes 406 and 408 therethrough. Board 410 allows electrical communication between components of device 400. In one embodiment, a resistor is disposed between electrodes 406 and 408 and the resistor produces a measurable voltage as current flows between the electrodes. In this case, the resistor is disposed on board 410 as well. A logic device or microchip is also disposed on board 410 and is in electrical communication with electrodes 406 and 408 and resistor. Functions of the logic device are described above and not described herein for sake of brevity.

In operation, chloride ions (Cl$^-$) penetrate inlet membrane 431 and cementitious membrane 429 from the surrounding environment. The chloride ions collect in electrolyte 427. With increasing concentration of chloride ions in electrolyte 427, silver ions precipitate from AgCl lead 427 into the calcium hydroxide solution. The silver ions build in concentration and migrate through permeable membrane 425 and into reservoir 407. With less silver ions on lead 427, the voltage between electrodes 406 and 408 changes and may be measured via the resistor disposed on board 410.

In one embodiment, electrodes 406 and 408 are pre-treated (aged) so that electrochemical drift or temporal inconsistency affecting sensor output is substantially prevented during the operating lifetime of the sensor. This may be performed for example, by exposing the electrode 406 to saturated calcium hydroxide solution (concrete pore solution is typically saturated Ca(OH)$_2$, so this effectively reproduces the initial bridge deck conditions) until any drift in electrode 406 performance has been alleviated. A period of about one hour to about several hundred hours of ion exposure may be suitable in some cases. In a specific embodiment, electrodes 406 and 408 are exposed to chloride ions for a period of about one day to about fourteen days.

For a roadway or bridge deck application, the volume for device 400 is derived from the size limitation on aggregates for high-strength concrete. Aggregate size is determined by many factors, including a) code requirements, b) thickness of the slab—aggregate size should generally be no more than about 25 percent of the thickness of the slab, and c) spacing of metal components. In some cases, aggregate size is determined by the desired compressive strength of the concrete. Higher strength concrete require smaller diameter aggregates. In a specific embodiment, device 400 has a generally accepted standard of ¾ inches (20 mm) diameter. A 20 mm diameter spherical aggregate has volume of 4.2 cm$^3$. For sensors of the present invention embedded in concrete when the concrete is poured, the device may have a specific gravity that keeps it from floating in the concrete mix. In some cases, an encapsulation around a sensor device of the present invention is compatible with the surrounding concrete mix or cement matrix. Some factors in this regard include shape, roughness, impact hardness, and compressive strength.

5. Alternative Sensors

Figure 5:
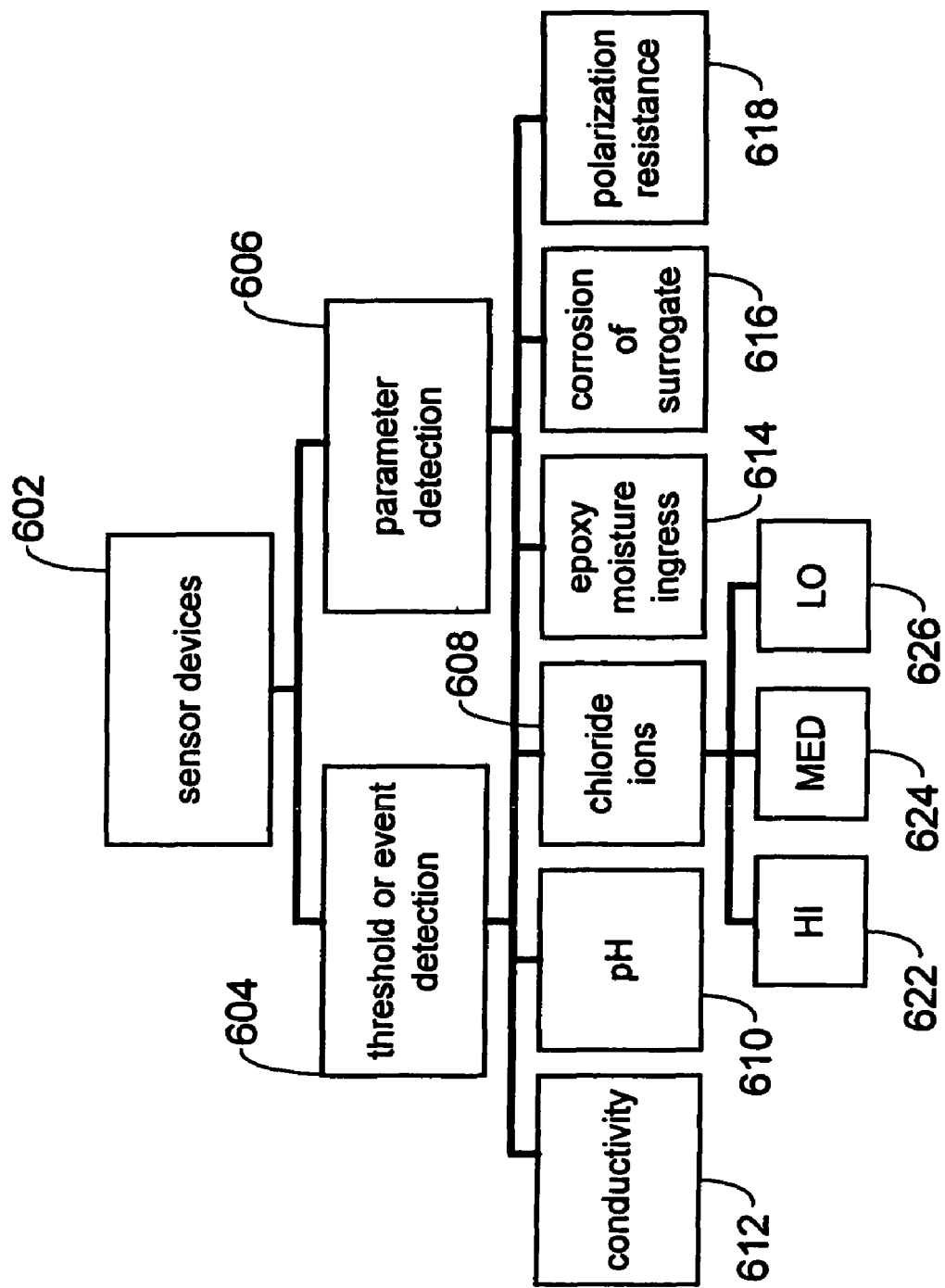
FIG. 5 illustrates an organization of sensor parameters useful for monitoring health of a structure in accordance with various embodiments of the present invention.

Although the present invention has primarily been described so far with respect to chloride ion concentration detection, sensor devices of the present invention may detect a wide variety of other parameters relevant to a structure's health. FIG. 5 illustrates an organization of sensor parameters useful for monitoring health of a structure in accordance with various embodiments of the present invention. As shown, sensor devices 602 of the present invention may be characterized by threshold or event detection 604 and parameter detection 606, such as real-time detection of a parameter.

There are a wide variety of parameters, threshold, and events that may be measured for sensors 602. As shown, threshold sensors 604 and parameter sensors 606 may include concentration sensors 608, pH sensors 610, conductivity sensors 612, epoxy moisture ingress sensors 614, corrosion of surrogate sensors 616, and polarization resistance sensors 618. One example of a concentration sensor 608 is a chloride ion sensor, which has been described in detail above. For example, a single chloride sensor may include three threshold levels: a high concentration level 622, a medium concentration level 624, and a low concentration level 626.

Each of the sensors described in FIG. 5 may use a configuration similar to one of the devices described above. For example, FIGS. 6A-6D illustrate various sensor devices that each detect a different parameter according to the sensor device embodiment shown in FIG. 4D. For each case, the device aside from the sensor remains substantially similar in basic components while the sensor has been replaced, and in a few cases, a few processing elements have been added or changed.

Figure 6A:
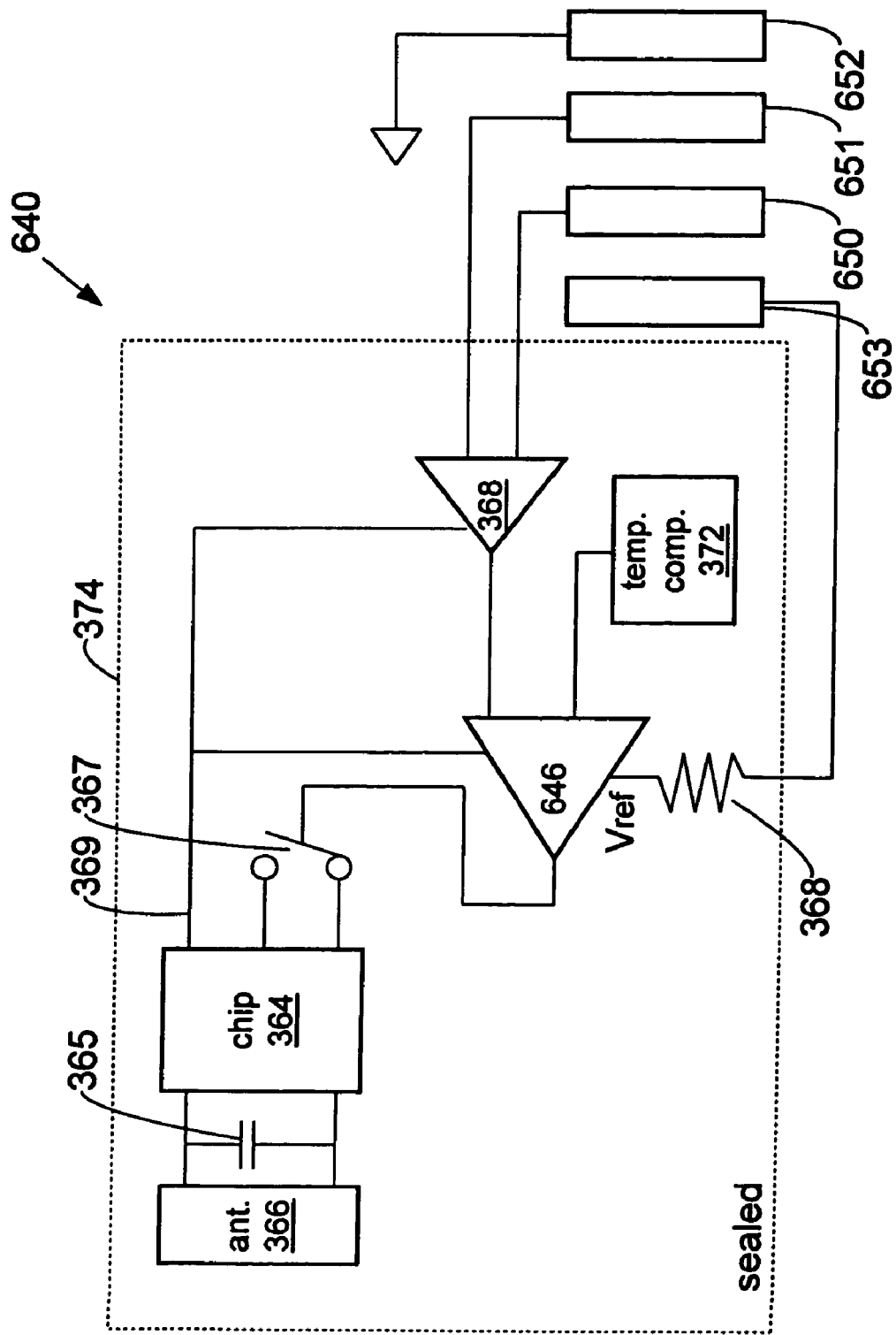
FIG. 6A illustrates a representative circuit for a sensor device that detects conductivity in accordance with one embodiment of the present invention.

FIG. 6A illustrates a representative circuit 640 for a sensor device that detects conductivity in accordance with one embodiment of the present invention. Circuit 640 comprises a conductivity sensor, microchip 364, antenna 366, micro-power operational amplifier 644, comparator 646, and temperature compensation circuitry 372. The conductivity sensor comprises four probes 650, 651, 652, and 654. All the components of circuit 640 except probes 650, 651, 652, and 654 are sealed within an interior cavity, as indicated by line 374. Chip 364, antenna 366, capacitor 365, seal 374, switch 367, and temperature compensation circuitry 372 are similar to that as described with respect to FIG. 4D.

Probes 650 and 651 are in electrical communication with a material whose conductivity is being measured, and provide a voltage difference to micro-power operational amplifier 644 based on the material's conductivity. Micro-power operational amplifier 644 converts the potential difference produced by probes 650 and 651 to a level suitable for comparison by comparator 646. Probe 652 is ground as a reference. Probe 653 is in electrical communication with current limiting resistor 648, which acts as a voltage reference for comparator 646. Comparator 646 compares the output of operational amplifier 644 with a threshold voltage, and factors in the output from temperature compensation circuitry 372. In one embodiment, comparator 646 is a nanowatt comparator that receives a reference voltage of 1.8 volts from current limiting resistor 648. Probes 650, 651, 652, and 654 may comprise stainless steel, copper, any metal that does not corrode in a concrete environment, or any other suitable conductive element. A sensor device comprising a conductivity sensor as shown in FIG. 6A is particularly useful to measure the conductivity of metal elements disposed in a structure whose conductivity changes with corrosion.

Figure 6B:
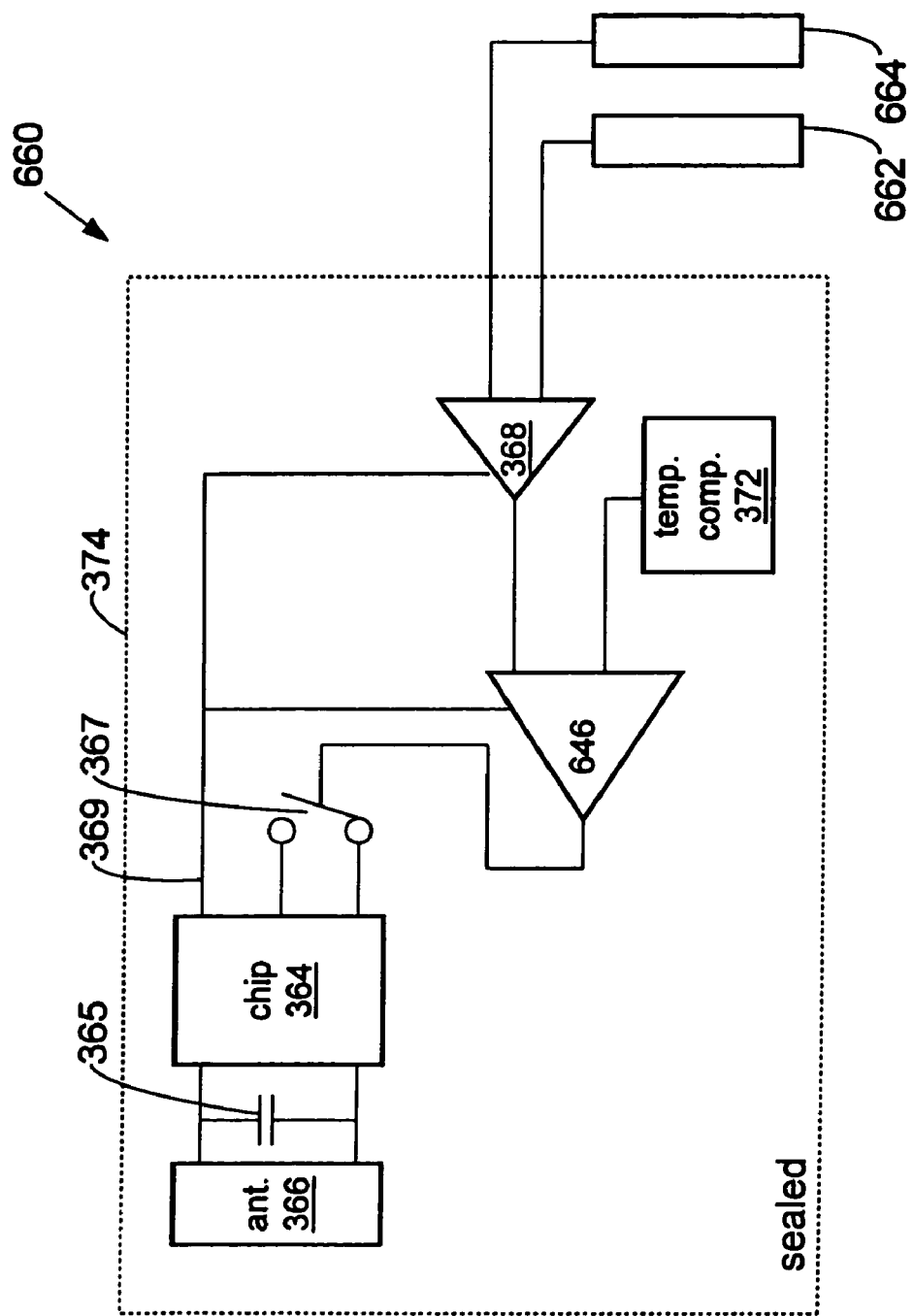
FIG. 6B illustrates a representative circuit for a sensor device that detects pH in accordance with another embodiment of the present invention.

FIG. 6B illustrates a representative circuit 660 for a sensor device that detects pH in accordance with another embodiment of the present invention. Circuit 660 comprises a pH sensor, microchip 364, antenna 366, micro-power operational amplifier 644, comparator 646, and temperature compensation circuitry 372. The pH sensor comprises two electrodes 662 and 664. Electrodes 662 and 664 are in ionic communication with a material whose pH is being measured, and provide a voltage difference to micro-power operational amplifier 644 based on the material's pH. Electrode 662 is a reference electrode, comprising $Cu/CuSO_4$ for example. Electrode 662 is an ion selective electrode, comprising Ni/NiO as an active element responsive to pH changes for example. A sensor device comprising a conductivity sensor as shown in FIG. 6B is particularly useful to measure pH of concrete in a structure whose pH changes over time.

Figure 6C:
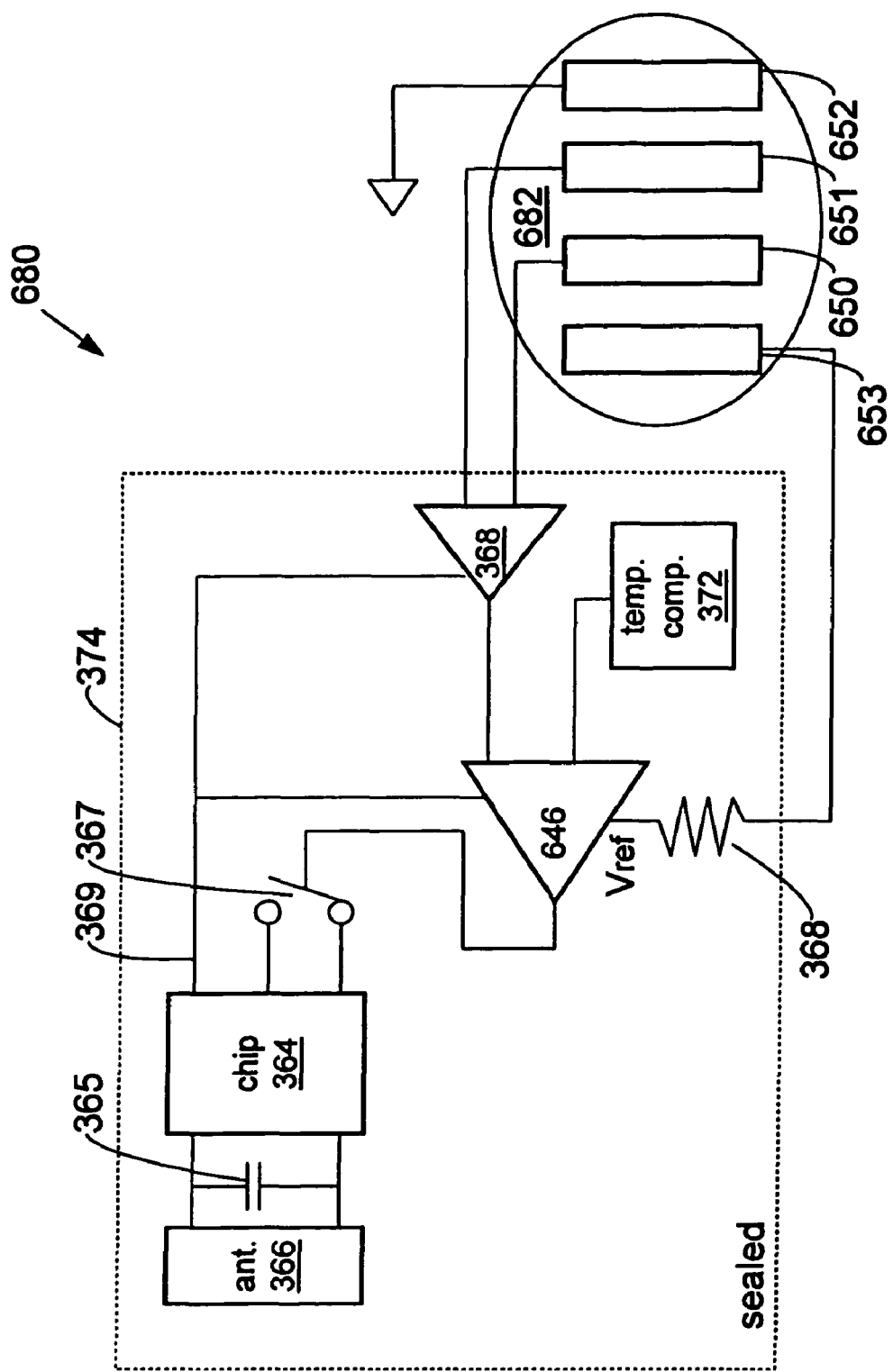
FIG. 6C illustrates a representative circuit for a sensor device that detects epoxy moisture ingress in accordance with one embodiment of the present invention.

FIG. 6C illustrates a representative circuit 680 for a sensor device that detects epoxy moisture ingress in accordance with one embodiment of the present invention. Circuit 680 is a conductivity sensor device similar to that as described with respect to FIG. 6A except that it measure the conductivity of an epoxy sample 682. Some metal elements in a bridge are protected by an epoxy disposed around the metal. In this case, a sensor device corresponding to representative circuit 680 is included to detect deterioration of the epoxy.

Figure 6D:
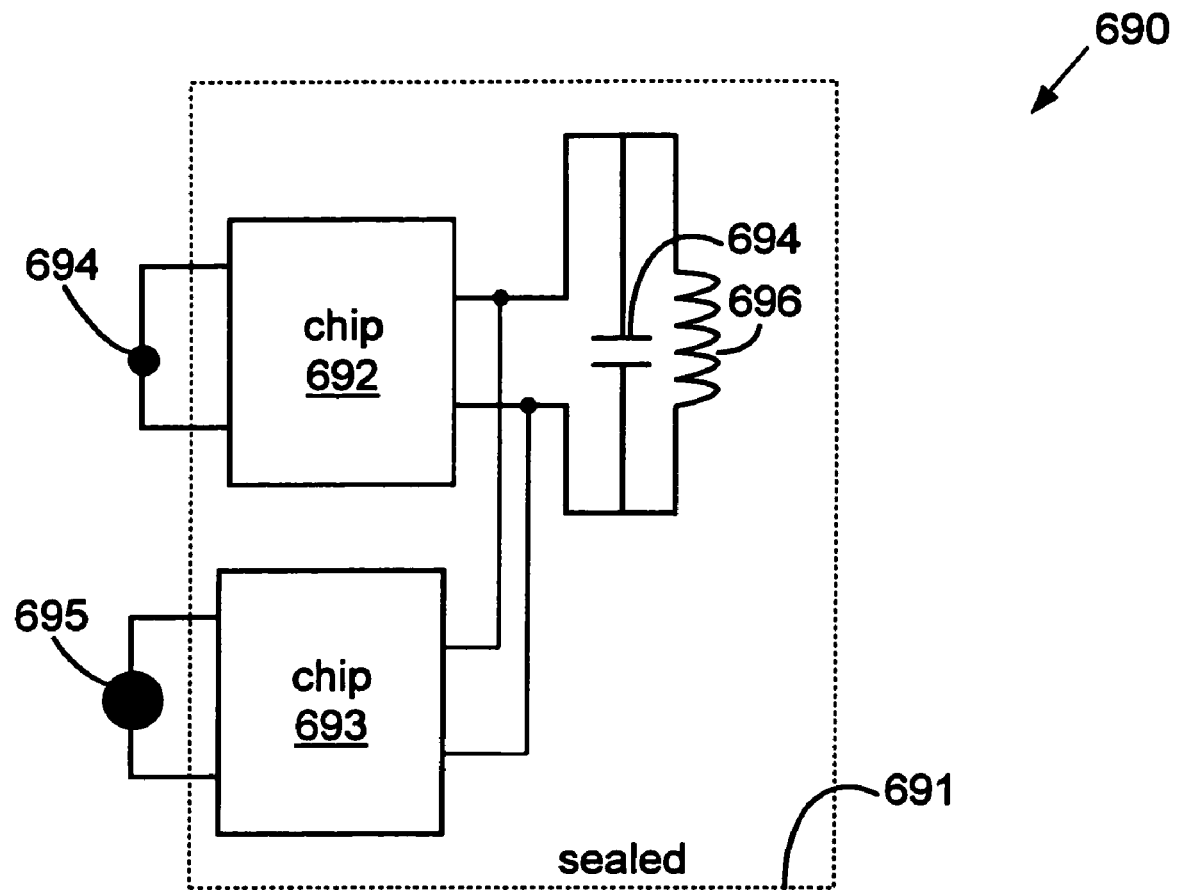
FIG. 6D illustrates a representative circuit for a sensor device that detects multiple corrosion events in accordance with another embodiment of the present invention.

FIG. 6D illustrates a representative circuit 690 for a sensor device that detects multiple corrosion events in accordance with another embodiment of the present invention. System 690 comprises chips 692 and 693, capacitor 694, wires 694 and 695, and antenna 696. All the components save wires 694 and 695 are sealed from the external environment as indicated by seal 691.

Wires 694 and 695 each act as a surrogate to a metal whose corrosion is being monitored. Each wire 694 and 695 has a diameter that indicates a corrosive level of interest. For example, wire 694 has a diameter $D_1$ and wire 695 has a diameter $D_2$, which is greater than $D_1$. Wires 694 and 695 are preferably the same material as the metal whose corrosion is being monitored and corrode corresponding to the metal being monitored. However, at some level of corrosive exposure, each wire 694 and 695 would corrode to the point at which it lost conductivity, or became open with respect to the microchip that it communicates with. The level of interest may correspond to a corrosive level below full corrosion of the metal being monitored, or substantially equal to full corrosion, for example.

The device corresponding to circuit 690 transmits an ID in response to a probing signal to determine when either corrosion event detected by wires 694 and 695 has occurred. More specifically, circuit 690 communicates corrosion of either surrogate wire 694 and 695 based on bit stream inversion of a microchip that each wire communicates with. Wire 694 is in electrical communication with microchip 692 and wire 695 is in electrical communication with microchip 693. Chips 692 and 693 provide binary feedback pertaining to whether wire 694 or 695 has corroded, based on an inversion of the ID code of each chip 692 and 693 when its respective wire 694 and 695 is open. In this case, an interrogator probing the sensor device distinguishes between the codes produced from each microchip. Suitable anticollision algorithms may also be used to prevent simultaneous response from each microchip 692 and 693. In a specific embodiment, chips 692 and 693 are a MCRF202 microchip as provided by Microchip Technology, Inc. of Chandler, Ariz.

Interrogators

An interrogator is used to probe a sensor device of this invention. The interrogator provides a wireless probe signal that triggers the sensor device to respond with its identity and a sensor reading (e.g., a parameter status). In one embodiment, the signal provided by the interrogator also provides the energy necessary for the sensor device to reply. The interrogator may be able to detect the reply and present that reply to a computer system or an individual conducting the analysis. Note that devices performing the functions of (1) energizing the sensor device and (2) communicating with the sensor device can be physically separate. They may use different signals for example. In one embodiment, the device produces multiple responses and the interrogator receives multiple signals. The first response may be ignored by the interrogator and the second is used as the response. The first response may be ignored due to uncertainty in the signal since elements in the sensor device may need time to reply (e.g., a capacitor).

As mentioned above, a wireless interrogation probe may take many different forms such as an RF signal, a microwave signal, an electric or magnetic field, etc. The transponder of the sensor device is designed to respond to type of signal provided by the interrogator. While it will often be convenient to design the interrogator and the sensor's transponder to send signals of the same type (e.g., both send RF signals), this is not a requirement of the invention. For example, the interrogator may provide a low-frequency magnetic field as a probe and the transponder may deliver the sensor information via a microwave signal.

An interrogator provides a probing signal (and power) to a sensor device. Preferably the interrogator includes sufficient radiated power to penetrate any structural material between the interrogator and the sensor device, sufficient radiated power to energize the device at the desired read rates, sufficient bandwidth to interrogate the device in a reasonable amount of time, sufficient sensitivity to accurately obtain the device response, sufficient specificity to discriminate between nearby devices (if desired based on the application), a suitable interface to a computer to record and update a database of sensor device history, a suitable size/weight/power limitation, suitable read range, and safety. An interrogator can accomplish sufficient radiated power to energize the device by transmitting an electromagnetic (DC, wave or field) or acoustic signal in the form of continuous wave, pulsed cir wave, chirped waveform, spread-spectrum waveform, impulse, or coded waveform to energize the tag. A specific embodiment employs a commercial product such as that supplied by Biomark (Destron) with modification to monitor sensed events. In one embodiment, conventional technology is used to produce the interrogator.

Figure 7:
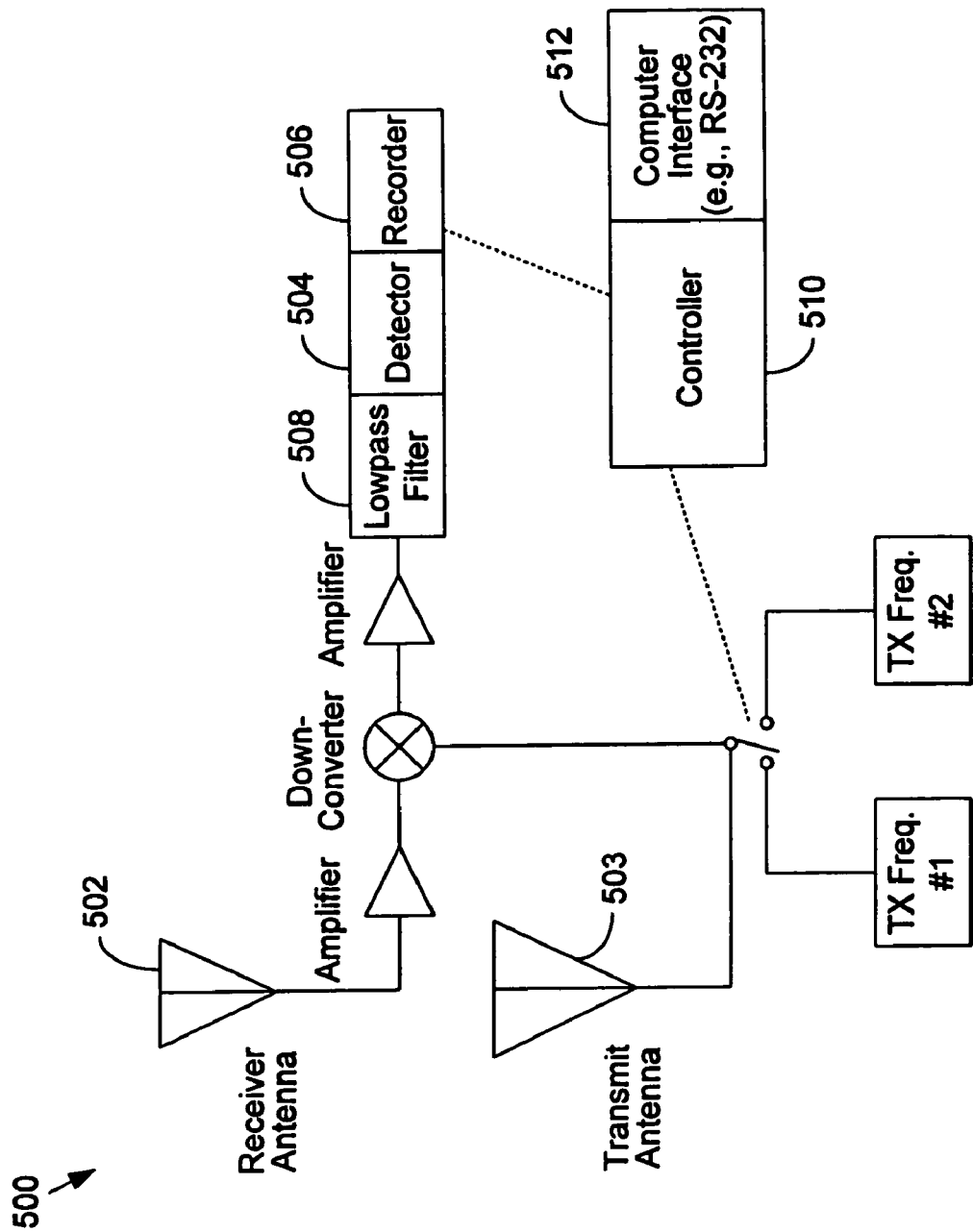
FIG. 7 illustrates an exemplary reader block diagram corresponding to an interrogator in accordance with one embodiment of the present invention.

FIG. 7 illustrates an exemplary reader block diagram corresponding to an interrogator 500 in accordance with one embodiment of the present invention. Interrogator 500 includes a receiver antenna 502 that is capable of receiving the resonant frequency of the one or more sensor devices it is polling. The interrogator 500 also includes a transmit antenna 503 that is capable of sending a suitable signal to the one or more devices it is polling. The transmit antenna 503 and the receiver antenna 502 may be combined if suitable isolation circuitry is used. The transmit frequency used to query the sensor device may also be used as a local oscillator in the homodyne receiver as illustrated. As mentioned in the description of FIG. 3A, a passive sensor device may rectify an incident RF signal coming from interrogator 500 to provide DC power for the microchip 342.

Once the microchip is activated, it modulates the incident carrier with the proper ID code and provides a modulated backscatter signal. The response signal may be at a frequency different from that of the incident signal. A remote receiver detector 504, which may be coupled to the interrogator, detects this modulated backscattered signal and records the ID information using recorder 506. Interrogator 500 may be used in conjunction with RFID sensor device 50 for example, in which the sensor device is capable of providing a differential frequency response for varying memory states of the sensor device 50. In this case, interrogator 500 is capable of receiving at a plurality of resonant frequencies (e.g., 103 kHz and 156 kHz). In addition, interrogator 500 includes one or more lowpass filters 508 as well as the detector 504 which are coupled to controller 510 and computer interface 512.

The choice of an operating frequency or frequencies may vary widely. For large arrays of sensor devices, regular or slightly modified commercially available equipment may provide cost savings. These devices operate in designated frequency bands such as 125 kHz, 13.56 MHz, 900 MHz, 2.45 GHz and 5.8 GHz. In some cases, RFID technology at 125 kHz is used due to its current maturity. Alternatively, it may be desirable to increase the interrogation frequency to increase the data rate and interrogation speed. Other criteria that may be used to select a frequency include penetration through structure materials such as concrete and other lossy, conductive or non-conductive media, improved read ranges and weight reduction.

In another embodiment of the present invention, interrogator 500 is configured to interrogate multiple sensor devices simultaneously. In this manner, interrogation of a large number of sensor devices may be expedited. For example, anti-collision RFIDs or algorithms that improve the ability of the interrogator to read multiple sensor devices are also suitable for use with the present invention. By way of example, a time domain multiple access (TDMA) system may be used in which a passive sensor responds with a time delay to interrogation.

A hand-held interrogator may also be used (FIG. 2A), and may poll multiple devices simultaneously. In another embodiment, the interrogator is non-stationary and transported by a vehicle such as that described with respect to FIG. 2B. For roadway inspection, having a vehicle carry the interrogator allows interrogation to occur without highway personnel leaving the vehicle and for interrogation to occur at moving vehicle speeds—further simplifying inspection and reducing inspection time.

It is also possible to use multiple interrogators to speed or otherwise improve inspection. These may be carried by multiple vehicles, or multiple interrogators may be placed on a single vehicle, for example. Regardless of the interrogator used for an application, the interrogator should have a suitable read range for probing the array of devices. By way of example, a hand held interrogator may have a read range from 1 inch to 12 inches. Higher read ranges also permit more devices to be probed simultaneously. Generally speaking, increased read ranges may be obtained by the use of increased interrogator power, increased size of the interrogator transmit antenna, increased size of the sensor device antenna, low power sensor device design (such as using components that make use of 3V logic instead of 5 V logic), increased size of the receiving antenna, and the use of shielding and interference mitigation strategies to improve reception capabilities and minimize signal leakage in the interrogator. In some cases, certain modulation and coding schemes for transponding data perform better in a noisy environment and these techniques are generally well known to those skilled in the art.

Regardless of the interrogator used, the interrogation process may be tuned to application specific requirements or to overcome application specific obstacles. Such obstacles include narrow-band and broad-band interference. To overcome weak signal reception from sensor devices in the presence of strong reader transmission, the interrogator may transmit short pulses and listen for sensor device echo when the transmitter is off. Alternatively, the interrogator may implement a sequence of isolation strategies to separate the receiver from the continuous wave transmission emissions. Physical separation, placement in pattern nulls and orthogonal polarization can achieve separation, for example. Transceiver-receiver isolation may also be achieved by the use of a high dynamic-range amplifier and mixer components and signal subtraction.

Figure 8:
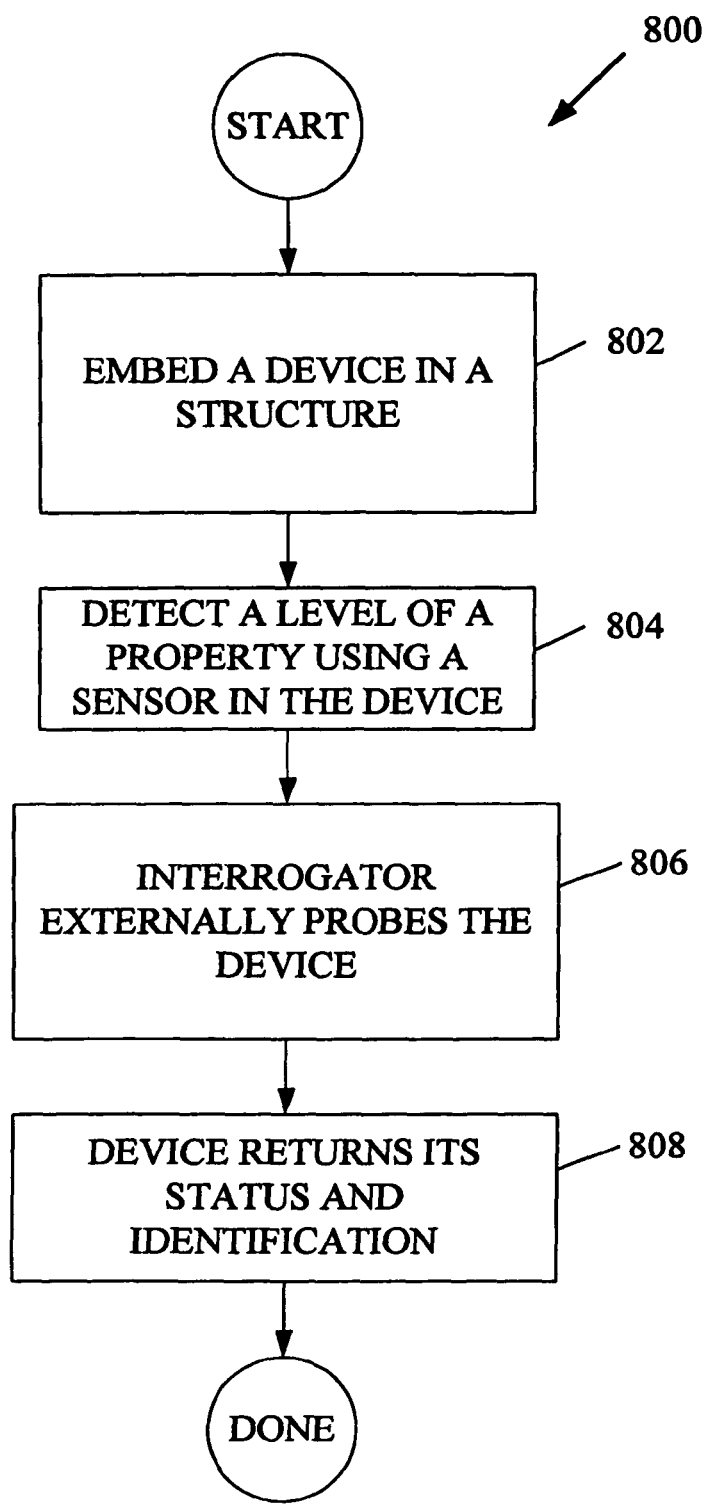
FIG. 8 is a process flow diagram depicting a typical procedure for using sensor devices and interrogators of this invention.

The general procedure involved in sensing and interrogation in accordance with this invention is depicted as process flow 800 of FIG. 8. The process flow 800 of FIG. 8 is particularly useful for monitoring the monitoring the health of a bridge comprising concrete and a metal.

Process flow 800 begins by embedding one or more sensor devices in the structure (802). The sensor device comprises a sensor that detects a parameter indicative of the health of the structure, an identification source that can distinguish the device from the other similar devices, and a transponder. In one embodiment, sensor devices of the present invention are employed within established roads and bridges by embedding the devices in back-filled cores (see FIG. 2B). In this case, the embedded sensors are inserted in the side wall of the core hole at various depths and permit estimation of chloride ingress at these depths. The core may be refilled with low porosity concrete (e.g., comprising polyester concrete) such that the sensors may measure chloride ingress through the extant structure. The sensor devices may also be embedded within new concrete to provide internal monitoring of chloride ion ingress and other chemical species penetration and attack. Immediately after installation in a new structure, the sensor devices should all respond negatively, that is, chloride concentration is below threshold limitations established for each device.

Subsequently, a sensor included in the device detects a parameter status (804) and is probed by an interrogator (806). This may occur in any order. For example, the sensor may make a sensor reading in response to a wireless probe from the interrogator. Alternatively, the sensor may periodically adapt based on the parameter being sensed (e.g., an evolving chemical change), and the interrogation signal probes the device at a later time. The interrogation signal may penetrate portions of the structure, as determined by the sensor device's position.

In response to the probe, the device returns a wireless signal (808). Similarly, the return signal may transmit through a portion of the structure. The return wireless signal indicates the parameter status. The return signal may also include an identification for the device. In one embodiment, the power incident on the sensor device is rectified to produce DC power used to operate the sensor device. Next, backscatter from the sensor device antenna (coil) is modulator by an RFID chip according to the ID code and sensor state in the sensor device memory. The transceiver demodulates the received backscatter and reports the ID and sensor reading to an associated computer. If desired, the computer may then update a database for the sensor device being monitored and flag a particular structural location corresponding to the sensor device position for further inspection and/or maintenance.

In one embodiment, a hand-held interrogator illuminates a local region, powering any embedded sensors in the region and obtaining data from the sensors. In another embodiment useful for bridge inspections, the interrogator is carried by a truck, or any other moving vehicle, and driven over the sensor.

If the system is provided with an array of sensor devices, an event or threshold may be proximate at least one of the sensor devices, which detects the physical or chemical event, while other sensor devices in the array do not detect the event. In some cases, after a sensor device is exposed to a condition of interest, it passively records the event using a recording mechanism. For example, the wires 692 and 693 may passively record corrosion levels by their irreversible corrosion and open circuit deterioration.

The interrogator may note the sensor information and other related information. If the reporting device is one of a group of related devices, the interrogator system may retrieve information identifying the spatial or temporal position of the reporting device within the group. The retrieved information may be provided in a database in which device location is keyed to device identification (ID tag information). Such a database is depicted within a system in FIG. 9.

Sensing (804), probing (806) and data return (808) may be repeated as desired by an application. Bridges for example are inspected biennially. Regular inspection also allows chloride ingress in a bridge to be tracked. Returning to FIG. 2B, is possible at a subsequent time that the top device 50$a$ indicates excess chloride concentration, but the remaining devices 50$b$-50$d$ indicate acceptable chloride concentration levels. The date of this measurement along with the known location of each device 50 provides a first estimate of the diffusion constant for this roadway or bridge deck. By correlating this information with known sensor depth and past history, chloride ingress progress may be tracked. As inspection continues over the years, highway personnel may track continued progress of chloride ingress as devices 50$b$-50$d$ deeper into roadway indicate chloride over limit conditions. And if chloride concentrations reach an over limit condition for sensor device 50$d$, more conclusive or additional action and may then be scheduled by highway personnel.

Applying this information collection over an entire bridge and hundreds of other bridges allows maintenance technicians to prioritize maintenance schedules for a large number of bridges. In addition, based on diffusion rate predictions from historical measurements, bridge treatment of hundreds or thousands of bridges in an area may be projected and prioritized based on quantitative data. Further, embedded sensors that provide chloride ion concentration measurement over time may also be used for detailed monitoring, regional comparisons, and research.

Sensor devices of the present invention may also monitor reversible and effective extraction of chloride from roadways and bridge decks. Remediation strategies are available to extract chloride out of bridge decks, such as electrochemical extraction of chloride.

The interrogation process illustrated in FIG. 8 is appropriate for some applications calling for a course inspection of a large structure followed by a fine examination of selected regions. The interrogation process involves a collection of devices (e.g., an array on a large structure with many devices such as a bridge. Initially, the structure is probed quickly to make sure that all devices are present and actually functioning. Next, the interrogator determines if any of the devices was exposed to the event of interest. This procedure may be performed without identifying specific devices in the collection. The interrogating signal may be chosen to identify frequencies that are characteristic of significant events, probing the entire structure (or at least a large region) all at once. The interrogator determines whether a "bad" response was detected. If such a bad response is detected, a more detailed inspection may be needed to determine the location of the device. If not, the process is complete. If the procedure finds that at least one device was exposed to the condition of interest, then a more involved interrogation may be performed, such as a manual inspection according to conventional analysis of core a sample.

The interrogation process illustrated in FIG. 8 may also include cross-referencing with a database, memory or other information storage mechanism. The database may be useful for storing information for a device based on its ID including the device's physical location or sensing history. A database is particularly appropriate when an array of sensor devices is probed.

In one embodiment to determine the location of the responding device, interrogator (or a related system) queries a database containing a list of device IDs and corresponding spatial locations. Database then responds with the location of the device identified in the query. This embodiment is particularly useful when the system includes an array of devices and interrogator determines which specific device within the array is reporting its status.

A cost-effective highway maintenance program may establish priorities based on the condition of each roadway and bridge being monitored. However, condition based maintenance requires routine roadway inspection to monitor degradation of the roadway and bridges surfaces and subsurfaces. When numerous devices are implemented in each roadway and bridge, the identification and state of each device may be stored in a database or otherwise recorded. The database allows a history for each device to be maintained. In the case of roadway inspection, the database also provides simple tracking of bridge health for a large number of bridges.

In a roadway and bridge health monitoring application, each individual sensor device may be identified as belonging to a unique location or known location relative in a roadway or bridge. In this application, where hundreds or thousands of individual devices may be implemented, the ID tag may include a 16 or 18 bit signal in which some bits are reserved for the sensor information and data and the remaining bits are reserved for identification of the individual device.

A computer-implemented user interface may be used to improve user analysis of an array of sensor devices. By way of example, a graphical user interface (GUI) may be used to help inspectors with roadway analysis. The roadway GUI may contain different colors for uninspected devices, inspected devices that read a particular concentration threshold, and inspected devices that did not record an event. In addition, the GUI allows the user to point a particular device in an array and obtain information on the device. The information may include the device's ID, location in the structure, and any history for the device as stored in a database. Any suitable GUI system suitable for integration with the reader coil may be used. In one specific embodiment, the GUI is implemented on a portable computing device (such as a Palm Pilot (3Com Corporation of Santa Clara, Calif.) or the like) to allow a user to view both the item under inspection and the computer display of the item.

Conclusion

The versatility, small size and wireless unobtrusive nature of the inventive remote sensor devices allow for sensor application in many interesting applications. Coupling the transponder and the sensor together allows for reduced weight and size. Further, the identification means of the inventive sensor devices allow for monitoring of systems where potentially thousands of sensors are implemented and each sensor may be individually monitored. While this invention has been described in terms of several preferred embodiments, there are alterations, permutations, and equivalents that fall within the scope of this invention which have been omitted for brevity's sake. It is therefore intended that the scope of the invention should be determined with reference to the appended claims.

What is claimed is:

1. A device comprising:
   an electrochemical cell comprising a reference electrode, an ion selective electrode, and an electrolyte, wherein the electrolyte is configured to provide a medium for movement of ions and to maintain an electrical connection between the reference electrode and the ion selective electrode;
   an enclosure including a permeable concrete membrane configured to allow an ion to pass into the electrolyte from outside of the device, wherein the enclosure contains the electrochemical cell;
   a sensor configured to determine a potential difference between the reference electrode and the ion selective electrode; and
   a transponder in electrical communication with the sensor, wherein the transponder is configured to transmit a wireless signal that includes the potential difference and an identifier associated with the device.

2. The device of claim 1, wherein the ion selective electrode is configured to respond to an ion that facilitates corrosion of a metal.

3. The device of claim 1, wherein the electrolyte is configured to maintain a consistent pH.

4. The device of claim 1, wherein the device is embedded in a structure, and wherein the wireless signal is configured to travel through at least a portion of the structure.

5. The device of claim 4, wherein the structure comprises concrete, and wherein the potential difference is indicative of a chloride ion concentration in the concrete.

6. The device of claim 1, wherein the device comprises a passive device.

7. The device of claim 1, further comprising:
   a temperature sensor configured to detect a temperature; and
   compensation circuitry configured to compensate the potential difference based at least in part on the temperature.

8. The device of claim 1, further comprising a memory configured to store the identifier, wherein the identifier is specific to the device.

9. The device of claim 1, wherein the wireless signal further includes an indication if the potential difference exceeds a threshold.

10. The device of claim 1, wherein the device is embedded in a structure, and wherein the potential difference is indicative of a health of the structure.

11. A system for monitoring a health of a structure, the system comprising:
    an array of devices, wherein each device in the array of devices is embedded in the structure, and wherein each device in the array of devices comprises:
       an electrochemical cell comprising a reference electrode, an ion selective electrode, and an electrolyte, wherein the electrolyte is configured to provide a medium for movement of ions between the reference electrode and the ion selective electrode;
       an enclosure including a port configured to allow the ions to pass into the electrolyte from outside of the device, wherein the port includes a permeable concrete membrane and the enclosure contains the electrochemical cell;
       a sensor configured to detect a parameter relating to the health of the structure and based at least in part on the ions that pass into the electrolyte; and
       a transponder in electrical communication with the sensor and configured to transmit a wireless signal to an interrogator, wherein the wireless signal includes the parameter and an identifier associated with the device; and
    the interrogator configured to receive the wireless signal.

12. The system of claim 11, wherein each device in the array of devices does not contain a power source.

13. The system of claim 12, wherein the interrogator is configured to power each device in the array of devices through a wireless interrogation signal, wherein the wireless interrogation signal is also configured to prompt the wireless signal from each device.

14. The system of claim 11, wherein the interrogator is configured to communicate with a database that includes the identifier associated with each device in the array of devices.

15. The system of claim 14, wherein the database comprises a set of records that identify a location of each device in the array of devices.

16. The system of claim 11, wherein the parameter comprises a quantity of or a state of a chemical species that affects the health of the structure.

17. The system of claim 11, wherein the interrogator is carried by a moving vehicle.

18. A method comprising:
embedding a sensor device in a structure, wherein the sensor device includes a sensor configured to detect a value of a parameter relating to a health of the structure, wherein the value of the parameter is based at least in part on ions in an electrolyte, and wherein the electrolyte is configured to provide a medium for movement of ions between a reference electrode of the sensor device and an ion selective electrode of the sensor device;
receiving an ion at the sensor device through a permeable concrete membrane of an enclosure configured to allow the ion to pass into the electrolyte from outside of the sensor device, wherein the enclosure contains the electrolyte;
detecting the value of the parameter using the sensor;
communicating the value of the parameter to an interrogator in response to a wireless interrogation signal received from the interrogator.

19. The method of claim 18, wherein the structure is a bridge or a portion of a bridge.

20. The method of claim 19, wherein the sensor device is embedded in concrete of the structure using a back filled core.

21. The method of claim 20, wherein the back filled core comprises a low porosity concrete.

22. The method of claim 18, wherein the interrogator is carried by a moving vehicle while communicating with the sensor device.

23. The method of claim 18, wherein the interrogator is carried by a person while communicating with the sensor device.

24. The method of claim 18, further comprising saving the value of the parameter in a database.

25. The method of claim 18, further comprising compensating the value of the parameter based at least in part on a temperature detected by the sensor device.

26. The method of claim 18, wherein the wireless interrogation signal further comprises power for the sensor device.

27. The method of claim 18, wherein the value of the parameter is communicated to the interrogator in a wireless signal, and wherein the wireless signal also includes an identifier associated with the sensor device.

* * * * *

UNITED STATES PATENT AND TRADEMARK OFFICE
CERTIFICATE OF CORRECTION

PATENT NO. : 7,986,218 B2  
APPLICATION NO. : 11/326224  
DATED : July 26, 2011  
INVENTOR(S) : Watters et al.

Page 1 of 1

It is certified that error appears in the above-identified patent and that said Letters Patent is hereby corrected as shown below:

Title page, item (75), under "Inventors", in Column 1, Line 5, delete "Jayaweeera," and insert -- Jayaweera, --.

Title Page 2, item (56), under "Other Publications", in Column 2, Line 5, delete "Structual" and insert -- Structural --.

Title Page 2, item (56), under "Other Publications", in Column 2, Line 7, delete "Structual" and insert -- Structural --.

Title Page 2, item (56), under "Other Publications", in Column 2, Line 9, delete "Tranducers" and insert -- Transducers --.

Title Page 2, item (56), under "Other Publications", in Column 2, Line 41, delete "Implatable" and insert -- Implantable --.

Title Page 2, item (56), under "Other Publications", in Column 2, Line 46, delete "Tranducers" and insert -- Transducers --.

Signed and Sealed this  
Twenty-seventh Day of December, 2011

David J. Kappos  
*Director of the United States Patent and Trademark Office*